United States Patent
Kurihara et al.

(10) Patent No.: US 11,478,539 B2
(45) Date of Patent: Oct. 25, 2022

(54) IMMUNITY-INDUCING AGENT

(71) Applicant: TORAY INDUSTRIES, INC., Tokyo (JP)

(72) Inventors: Akira Kurihara, Kamakura (JP); Fumiyoshi Okano, Kamakura (JP)

(73) Assignee: Toray Industries, Inc., Tokyo (JP)

(*) Notice: Subject to any disclaimer, the term of this patent is extended or adjusted under 35 U.S.C. 154(b) by 219 days.

(21) Appl. No.: 16/746,204

(22) Filed: Jan. 17, 2020

(65) Prior Publication Data

US 2020/0138926 A1    May 7, 2020

Related U.S. Application Data

(62) Division of application No. 15/567,448, filed as application No. PCT/JP2016/063436 on Apr. 28, 2016, now abandoned.

(30) Foreign Application Priority Data

Apr. 30, 2015  (JP) ............................. JP2015-093354

(51) Int. Cl.
*A61K 39/00* (2006.01)
*A61K 35/15* (2015.01)
(Continued)

(52) U.S. Cl.
CPC .. *A61K 39/001174* (2018.08); *A61K 31/7088* (2013.01); *A61K 35/15* (2013.01);
(Continued)

(58) Field of Classification Search
CPC ........ A61K 35/17; A61K 39/00; A61K 48/00; A61K 2039/5154; A61K 2039/5158; A61P 35/00; A61P 35/02
See application file for complete search history.

(56) References Cited

U.S. PATENT DOCUMENTS 5,698,396 A    12/1997  Pfreundschuh
2011/0123492 A1*  5/2011  Okano ................. C12N 5/0636
                                                      424/85.2
(Continued)

FOREIGN PATENT DOCUMENTS

JP    9-194502 A    7/1997
JP    2000-95795 A  4/2000
(Continued)

OTHER PUBLICATIONS

Hafner et al., Adv Drug Delivery Rev, 65:1386-1399, 2013 (Year: 2013).*
(Continued)

*Primary Examiner* — Lei Yao
(74) *Attorney, Agent, or Firm* — Birch, Stewart, Kolasch & Birch, LLP

(57) ABSTRACT

This application provides an immunity-inducing agent comprising, as an active ingredient, at least one polypeptide having immunity-inducing activity and selected from (a) polypeptides consisting of amino acid sequences represented by SEQ ID NO: 8, 4, 6, 10, 12, 2 and 14, and polypeptides consisting of 7 or more consecutive amino acids in the amino acid sequences, (b) polypeptides having a sequence identity of 85% or more with the amino acid sequences represented by SEQ ID NO: 8, 4, 6, 10, 12, 2 and 14, and polypeptides consisting of 7 or more consecutive amino acids in the amino acid sequences, and (c) polypeptides comprising the polypeptides according to (a) or (b) as the partial sequences, or a recombinant vector comprising a polynucleotide encoding the polypeptide and capable of expressing the polypeptide in vivo.

10 Claims, 3 Drawing Sheets

Specification includes a Sequence Listing.

(51) Int. Cl.
*A61K 35/17* (2015.01)
*A61K 48/00* (2006.01)
*A61K 31/7088* (2006.01)
*A61P 35/02* (2006.01)
*A61P 35/00* (2006.01)

(52) U.S. Cl.
CPC .............. *A61K 35/17* (2013.01); *A61K 39/00* (2013.01); *A61K 48/00* (2013.01); *A61P 35/00* (2018.01); *A61P 35/02* (2018.01); *A61K 2039/5154* (2013.01); *A61K 2039/5158* (2013.01); *A61K 2039/53* (2013.01); *A61K 2039/572* (2013.01)

(56) References Cited

U.S. PATENT DOCUMENTS

| | | |
|---|---|---|
| 2012/0177673 A1 | 7/2012 | Kurihara et al. |
| 2014/0120059 A1 | 5/2014 | Kurihara et al. |
| 2014/0154206 A1 | 6/2014 | Kurihara et al. |

FOREIGN PATENT DOCUMENTS

| | | | |
|---|---|---|---|
| JP | 2003-79374 A | | 3/2003 |
| WO | WO 2006/091861 A2 | | 8/2006 |
| WO | WO2006091861 | * | 8/2006 |
| WO | WO 2010/016525 A1 | | 2/2010 |
| WO | WO 2011/027807 A1 | | 3/2011 |
| WO | WO 2012/157736 A1 | | 11/2012 |
| WO | WO 2012/157737 A1 | | 11/2012 |

OTHER PUBLICATIONS

Kinugasa et al., BBRC 321: 1045-49 2004 (Year: 2004).*
Aono et al., "Expression and Identification of a New Splice Variant of Neuroglycan C, a Transmembrane Chondroitin Sulfate Proteoglycan, in the Human Brain", Journal of Neurosci. Res. 83: 110-118 (2006).
Extended European Search Report dated Nov. 21, 2018, in European Patent Application No. 16786585.6.
Fujii et al., "1. Gan Kogen Vaccines", Experimental Medicine, 2013, vol. 31, No. 12, pp. 142-147.
Hafner et al., "Particulate formulations for the delivery of poly(I:C) as vaccine adjuvant," Advanced Drug Delivery Reviews (2013), vol. 65, pp. 1386-1399.
International Search Report, issued in PCT/JP2016/063436, PCT/ISA/210, dated Jun. 28, 2016.
Kinugasa et al., "Neuroglycan C, a novel member of the neuregulin family", Biochem. Biophys. Res. Commun 321: 1045-1099 (2004).
Nakanishi et al., "Identification of Neurite Outgrowth-promoting Domains of Neuroglycan C, a Brain-specific Chondroitin Sulfate Proteoglycan, and Involvement of Phosphatidylinositol 3-Kinase and Protein Kinase C Signaling Pathways in Neuritogenesis", J. Biol. Chem., 281, No. 34, pp. 24970-24978 (2006).
Press et al., "Identification of a Preneoplastic Gene Expression Profile in Tubal Epithelium of BRCA1 Mutation Carriers 1,2,3", Neoplasia. vol. 12 (12): 993-1002 (2010).
Riccardo et al., "CSPG4-Specific Immunity and Survival Prolongation in Dogs with Oral Malignant Melanoma Immunized with Human CSPG4 DNA," Clin. Cancer Res. (Jul. 15, 2014), vol. 20, No. 14, pp. 3753-3762.
Sahin et al., "Human neoplasms elicit multiple specific immune responses in the autologous host", Proc. Natl. Acad. Sci. USA, 92: 11810-11813 (1995).
Van Der Bruggen et al., "A gene Encoding an Antigen Recognized by Cytolytic T Lymphocytes on a Human Melanoma", Science, 254:1643-1647, (1991).
Watanabe et al., "Neuroglycan C, a Novel Membrane-spanning Chondroitin Sulfate Proteoglycan That Is Restricted to the Brain", The Journal of Biological Chemistry, Nov. 10, 1995, vol. 270, No. 45, p. 26876-26882.
Written Opinion of the International Searching Authority, issued in PCT/JP2016/063436, PCT/ISA/237, dated Jun. 28, 2016.
Wu et al., "Expression of ErbB Receptors and their Cognate Ligands in Gastric and Colon Cancer Cell Lines", Anticancer Research, 2009, vol. 29, No. 1, p. 229-234.
Yasuda et al., "Cloning and chromosomal mapping of the human gene of neuroglycan C (NGC), a neural transmembrane chondroitin sulfate proteoglycan with an EGF module", Neurosci. Res. 32: 313-322(1998).
Yip et al., "Immunohistochemical Analysis of CSPG5: A Novel Prognostic Factor for Breast Cancer," Breast & 13th St. Gallen International Breast Cancer Conference; St. Gallen, Switzerland, Mar. 13-16, 2013, vol. 22, No. Suppl. 1, p. S34 (abstract).

* cited by examiner

IMMUNITY-INDUCING AGENT

CROSS-REFERENCE TO RELATED APPLICATIONS

This application is a Divisional of copending application Ser. No. 15/567,448, filed on Oct. 18, 2017, which is the National Phase under 35 U.S.C. § 371 of International Application No. PCT/JP2016/063436, filed on Apr. 28, 2016, which claims the benefit under 35 U.S.C. § 119(a) to Patent Application No. 2015-093354, filed in Japan on Apr. 30, 2015, all of which are hereby expressly incorporated by reference into the present application.

TECHNICAL FIELD

The present invention relates to a novel immunity-inducing agent that useful s a therapeutic and/or preventive agent or the like for cancers.

The present invention also relates to an antigen-presenting cell or a cytotoxic T cell for use in cancer immunotherapy, or, to a method for preparing the cells.

BACKGROUND ART

Cancer is the overall leading cause of death. At present, the primary form of cancer treatment technique is surgical treatment, which is carried out in combination with radiation treatment and chemotherapy. In spite of the development of novel surgical techniques and the discovery of novel anti-cancer agents of recent years, outcomes from cancer treatment still remain unimproved, except in the cases of some types of cancers. In recent years, cancer antigens recognized by cytotoxic T cells that are reactive to cancer and genes encoding cancer antigens have been identified along with the development of molecular biology and cancer immunology, and expectations for antigen-specific immunotherapy have increased.

Immunotherapy requires the cancer-cell-specific presence of a peptide, polypeptide, or protein that is recognized as a target antigen, as well as substantial absence thereof in normal cells from the viewpoint of alleviation of side effects. In 1991, Boon et al. (the Ludwig Institute for Cancer Research, Belgium) isolated the human melanoma antigen MAGE1 recognized by the CD8+ T cell via cDNA expression cloning using an autologous cancer cell line and cancer-reactive T cells (Non Patent Literature 1). Thereafter, the SERER (serological identification of antigens by recombinant expression cloning) method, which identifies the tumor antigen recognized by the antibody produced in response to autologous cancer in the body of a cancer patient via gene expression cloning was reported (Patent Literature 1, Non Patent Literature 2), Some cancer antigens have been isolated by such techniques. In addition, clinical tests of cancer immunotherapy targeting some of such cancer antigens have been initiated.

As in the case of humans, dogs and cats are known to suffer from a variety of tumors, such as mammary gland cancer and squamous cell carcinoma, and tumors are highly ranked in statistics for canine or feline diseases. However, there are no effective therapeutic, preventive, or diagnostic agents for canine or feline cancer at present. Most dog or cat owners would not notice canine or feline tumors until tumors become advanced and enlarged. Even if tumors are removed via surgical operation or drugs for human use (e.g., anticancer drugs) are administered, tumors are often already beyond cure, and animals often die shortly after treatment. Under such circumstances, if therapeutic, preventive, and diagnostic agents for cancer that are effective for dogs or cats become available, application thereof for canine or feline cancer can be expected.

Chondroitin Sulfate Proteoglycan 5 (CSPG5) is type 1 transmembrane protein and is one of the neuregulin family proteins. It is also reported that CSPG5 binds ErbB3 to act as a growth factor; and that the expression of CSPG5 increases in the ovarian cancer having a BRCA1 mutation (Non Patent Literatures 3 and 4). It is further known that CSPG5 is highly expressed in tissues of the nervous system such as retinal ganglion cells, purkinje cells and hippocampus, and serves as a proliferation/differentiation factor of nerve cells involved in elongation of nerve axons (Non Patent Literatures 5, 6, and 7). However, there have been no reports that the CSPG5 protein has an immunity-inducing activity against cancer cells and thus is useful for treating and preventing cancers.

CITATION LIST

Patent Literature

Patent Literature 1: U.S. Pat. No. 5,698,396

Non Patent Literatures

Non Patent Literature 1: Bruggen, P. et al., Science, 254: 1643-1647 (1991)
Non Patent Literature 2: Sahin, U et al., Proc. Natl. Acad. Sci. USA, 92: 11810-11813 (1995)
Non Patent Literature 3: Kinugasa, Y. et al., Biochem. Biophys. Res. Commun 321: 1045 (2004)
Non Patent Literature 4: Press, J Z. et al., Neoplasia. December; 12 (12): 993-1002. (2010)
Non Patent Literature 5: Yasuda, Y. et al., Neurosci. Res. 32: 313 (1998)
Non Patent Literature 6: Aono, S. et al., J. Neurosci. Res. 83: 110 (2006)
Non Patent Literature 7: Nakanishi, K. et al., J. Biol. Chem. 281: 24970 (2006)

SUMMARY OF INVENTION

Technical Problem

It is an object of the present invention to find a novelpolypeptide useful for a therapeutic and/or preventive agent for cancer and to provide use of such polypeptide as an immunity-inducing agent.

Solution to Problem

The present inventors conducted intensive studies, and as a result, have now obtained a cDNA encoding a protein binding to an antibody present in sera from cancer-bearing living bodies by the SEREX method using a cDNA library derived from the canine testis along with sera of cancer-bearing dogs. Based on the cDNA, the present inventors prepared a polypeptide of canine Chondroitin Sulfate Proteoglycan 5 (hereinafter referred to as "CSPG5") having the amino acid sequence represented by SEQ ID NO: 2. Furthermore, based on human, cat and mouse homologous genes to the obtained gene, they prepared CSPG5 polypeptides of a human, cat and mouse having the amino acid sequences represented by SEQ ID NOs: 4, 6, 8, 10, 12, 14 and 16. The present inventors have now also found that these CSPG5 polypeptides are specifically expressed in tissues or cells of breast cancer, lung cancer, brain tumor, ovarian cancer, leukemia, malignant lymphoma, adenocarcinoma, mastocytoma, squamous cell carcinoma, melanoma or neuroblastoma. Furthermore, they have now further found that immune cells against CSPG5 can be induced in vivo by administering these CSPG5 to living bodies, and that the size of a tumor in the living bodies where CSPG5 is expressed can be reduced. Moreover, they have now found that a recombinant vector capable of expressing a polynucleotide encoding CSPG5 polypeptide or a fragment thereof induces an antitumor effect on a CSPG5 expressing cancer in vivo.

The present inventors have now also found that the CSPG5 polypeptide is presented by an antigen-presenting cell and has an ability (i.e., an immunity-inducing activity) to activate and proliferate a cytotoxic T cell specific to the polypeptide; that the polypeptide is useful for treating and/or preventing cancers because of the ability; and that the antigen-presenting cell, which was in contact with the polypeptide, and the T cell, which was in contact with the antigen-presenting cell, are useful for treating and/or preventing cancers. Based on the findings, the present invention was accomplished.

Accordingly, the present invention has the following features.

(1) An immunity-inducing agent comprising, as an active ingredient, (i) at least one polypeptide having immunity-inducing activity and selected from the following polypeptides (a), (b), and (c), or (ii) a recombinant vector comprising a polynucleotide encoding the polypeptide and capable of expressing said polypeptide in vivo:
  (a) a polypeptide consisting of the amino acid sequence represented by SEQ ID NO: 8, 4, 6, 10, 12, 2 or 14, and a polypeptide consisting of 7 or more consecutive amino acids in the amino acid sequence;
  (b) a polypeptide having a sequence identity of 85% or more with the amino acid sequence represented by SEQ ID NO: 8, 4, 6, 10, 12, 2 or 14, and a polypeptide consisting of 7 or more consecutive amino acids in the amino acid sequence of the polypeptide;
  (c) a polypeptide comprising the polypeptide (a) or (b) as a partial sequence.
(2) The immunity-inducing agent according to (1), wherein the polypeptide having immunity-inducing activity is a polypeptide consisting of the amino acid sequence represented by SEQ ID NO: 8, 4, 6, 10, 12, 2 or 14.
(3) The immunity-inducing agent according to (1) or (2), which is for use in treating an antigen-presenting cell.
(4) The immunity-inducing agent according to (1) or (2), which is for use in treating and/or preventing cancer.
(5) The immunity-inducing agent according to (4), wherein the cancer is a CSPG5 expressing cancer.
(6) The immunity-inducing agent according to (4) or (5), wherein the cancer is brain tumor, leukemia, malignant lymphoma or neuroblastoma.
(7) The immunity-inducing agent according to any one of (1) to (6), further comprising an immunoenhancer.
(8) The immunity-inducing agent according to (7), wherein the immunoenhancer is at least one selected from the group consisting of Freund's incomplete adjuvant, Montanide, Poly IC and derivatives thereof, CpG oligonucleotides, interleukin 12, interleukin 18, interferon α, interferon β, interferon ω, interferon γ, and Flt 3 ligand.
(9) A method for preparing an antigen-presenting cell containing a complex of the polypeptide defined in (1) and an MEW molecule, comprising contacting the polypeptide with an antigen-presenting cell from a subject ex vivo or in vitro.
(10) The method according to (9), wherein the antigen-presenting cell is a dendritic cell or B cell having an MEW class I molecule.
(11) A method for preparing a cytotoxic T cell specific to the polypeptide defined in (1), comprising contacting the antigen-presenting cell obtained by the method according to (9) or (10) with a T cell from a subject ex vivo or in vitro, thereby activating the T cell.
(12) An antigen-presenting cell obtained by the method according to (9) or (10) and containing a complex of the polypeptide defined in (1) and a MHC molecule.
(13) A cytotoxic T cell obtained by the method according to (11) and specific to the polypeptide defined in (1).

The description includes the contents disclosed in JP Patent Application No. 2015-093354 from which the present application claims the priority.

According to the present invention, there is provided a novel immunity-inducing agent useful for, treatment and/or prevention or the like of cancers. When the polypeptide or the vector encoding the polypeptide used in the invention is administered to a subject, immune cells can be induced in the living body of the subject and a cancer which has already occurred can be reduced in size or regressed, as specifically shown in Examples described later. Thus, the polypeptide or the vector is useful for treating and preventing cancers.

DESCRIPTION OF EMBODIMENTS

Figure 1:
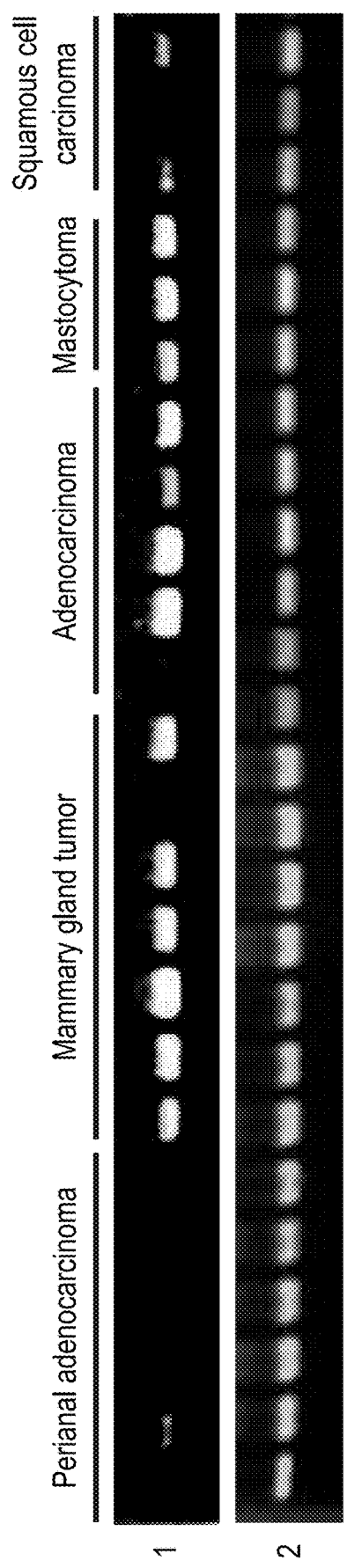
FIG. 1 This figure shows expression patterns of CSPG5 gene identified in canine tumor tissues or cancer cell lines. Reference number 1 shows expression patterns of the canine CSPG5 gene in individual canine tissues and cell lines; and reference number 2 shows expression patterns of canine GAPDH gene in individual canine tissues and cell lines.

The present invention will be more specifically described.
1. Polypeptide

As a polypeptide having immunity-inducing activity and contained as an active ingredient in the immunity-inducing agent of the present invention, polypeptides defined in the following (a) to (c) are included:
  (a) a polypeptide consisting of the amino acid sequence represented by SEQ ID NO: 8, 4, 6, 10, 12, 2 or 14, or a polypeptide consisting of 7 or more consecutive amino acids in the amino acid sequence;
  (b) a polypeptide having a sequence identity of 85% or more with the amino acid sequence represented by SEQ ID NO: 8, 4, 6, 10, 12, 2 or 14, or a polypeptide consisting of 7 or more consecutive amino acids in the amino acid sequence of the polypeptide;
  (c) a polypeptide comprising the polypeptide (a) or (b) as a partial sequence.

Herein the term "polypeptide" refers to a molecule formed of a plurality of amino acids which are bound via peptide linkage, and includes not only a polypeptide molecule constituted of a large number of amino acids but also a low molecular-weight molecule (i.e., an oligopeptide) constituted of a small number of amino acids, or a full-length protein. In the present invention, the full-length CSPG5 protein having the amino acid sequence represented by SEQ ID NO: 8, 4, 6, 10, 12, 2 or 14 is also included.

Herein the phrase "having an(the) amino acid sequence" means that amino acid residues align in the order shown in the amino acid sequence, unless otherwise specified. Accordingly, for example, the "polypeptide having the amino acid sequence represented by SEQ ID NO: 8" refers to a polypeptide having a size of 566 amino acid residues and consisting of the amino acid sequence of Met Gly Arg Ala, Gly . . . (omission) . . . Asn, Asn, Leu and Thr represented by SEQ ID NO: 8. The "polypeptide having the amino acid sequence represented by SEQ ID NO: 8" is sometimes simply referred to as, for example, "the polypeptide of SEQ ID NO: 8". The same is applied to the expression "having a(the) nucleotide sequence". In the phrase "having an(the) amino acid sequence" or "having a(the) nucleotide sequence", the term "having" may be replaced by the term "consisting of", unless otherwise specified.

Herein the term "immunity-inducing activity" refers to an ability to induce immune cells secreting cytokines such as interferon in the living body of a subject.

Herein the term "subject" refers to an animal in need of induction of immunity for treating or preventing a cancer (or tumor) by the immunity-inducing agent of the present invention, preferably refers to a mammal including a human, a pet animal such as dog or cat, an animal such as panda raised in zoo, a farm animal such as cow and racing animal such as horse.

Whether or not the polypeptide above has an immunity-inducing activity can be confirmed by using, for example, ELISpot Assay (Enzyme-Linked ImmunoSpot Assay) known in the art. More specifically, for example, as described in Examples below, the immunity-inducing activity can be evaluated by: obtaining cells like peripheral blood mononuclear cells from an animal to which the polypeptide to be evaluated for immunity-inducing activity has been administered; co-culturing the cells with the polypeptide; and measuring the amount of a cytokine produced from the cells by using a specific antibody, thereby determining the number of immune cells in the cells.

As described in Examples below, when the polypeptides of the above (a) to (c) (preferably, recombinant polypeptide) each are administered to cancer-bearing living bodies, tumors can be regressed due to the immunity-inducing activity of the polypeptides. Accordingly, the immunity-inducing activity can be evaluated as an ability to suppress proliferation of cancer cells or reduce the size of a cancer tissue (tumor) or eliminate a cancer tissue (tumor) (hereinafter referred to as "antitumor activity"). The antitumor activity of a polypeptide can be confirmed by actually administering the polypeptide to cancer-bearing animals and examining, for example, whether or not a tumor is reduced in size, for example, as specifically described in Examples below. Alternatively, the antitumor activity of a polypeptide may be evaluated by examining, for example, whether a cytotoxic T cell, which is induced by administering the polypeptide to cancer-bearing animals, exhibits cytotoxic activity to a tumor. The cytotoxic activity of a T cell can be determined in vivo by administering an antibody, which removes the T cell from a living body, to cancer-bearing animals and examining whether or not a tumor is reduced in size. However, the method of determining cytotoxic activity is not limited to those mentioned above.

Alternatively, the antitumor activity of the above-mentioned polypeptides may be evaluated by examining whether or not T cells stimulated with the polypeptides (more specifically, T cells contacted with antigen-presenting cells that present the polypeptides) exhibit cytotoxic activity against tumor cells in vitro. The T cells and the antigen-presenting cells may be contacted with each other by co-culturing both cells in a liquid medium, as described later. The cytotoxic activity may be measured by the known method called $^{51}$Cr release assay, for example, described in D. D. Kharkevitch et al., Int. J. Cancer, 58: 317-323, 1994. When the above-mentioned polypeptides are used for treatment and/or prevention of cancers, the immunity-inducing activity is preferably evaluated by using the antitumor activity as an indicator although such evaluation is not particularly limited thereto.

In the present invention, the amino acid sequences represented by SEQ ID NOs: 8, 4, 6, 10, 12, 2 and 14 as described in the Sequence Listing are the amino acid sequences of CSPG5, which were isolated, as the polypeptides that bind to specific antibodies present in the sera derived from cancer-bearing dogs, by the SEREX method using a cDNA library derived from canine testis and the sera of cancer-bearing dogs, and as homologous factors from human, cat, and mouse (see, Example 1). Human CSPG5, which is a human homolog homologous with dog CSPG5, has a nucleotide sequence identity of 87% and an amino acid sequence identity of 87%. Cat CSPG5, which is a cat homolog, has a nucleotide sequence identity of 92% and an amino acid sequence identity of 91%. Mouse CSPG5, which is a mouse homolog, has a nucleotide sequence identity of 84% and an amino acid sequence identity of 85%.

The polypeptide defined in the (a) above is a polypeptide which consists of 7 or more consecutive amino acids, preferably 8, 9 or 10 or more consecutive amino acids in the polypeptide having the amino acid sequence represented by SEQ ID NO: 8, 4, 6, 10, 12, 2 or 14, and which has an immunity-inducing activity. More preferably, the polypeptide consists of an amino acid sequence having a sequence identity of 85% or more with the amino acid sequence represented by SEQ ID NO: 8; and particularly preferably, the polypeptide has the amino acid sequence represented by SEQ ID NO: 8, 4, 6, 10, 12, 2 or 14. As known in the art, if a polypeptide has about 7 or more amino acid residues, then the polypeptide can exhibit antigenicity and immunogenicity. As such, where the polypeptide has 7 or more consecutive amino acid residues in the amino acid sequence represented by SEQ ID NO: 8, 4, 6, 10, 12, 2 or 14, it can possess an immunity-inducing activity and thus can be used for preparation of the immunity-inducing agent of the invention.

As the principle of immune induction by administration of a cancer antigenic polypeptide, the following; process is known: a polypeptide is incorporated into an antigen-presenting cell and then degraded into smaller fragments by peptidases in the cell, followed by presentation of the fragments on the surface of the cell. The fragments are then recognized by a cytotoxic T cell or the like, which selectively kills cells presenting the antigen. The size of the polypeptide presented on the surface of the antigen-presenting cell is relatively small and is about 7 to 30 amino acids. Therefore, from the viewpoint of presenting the polypeptide on the surface of the antigen-presenting cell, one preferred mode of the above-described polypeptide (a) is a polypeptide composed of about 7 to 30 consecutive amino acids in the amino acid sequence represented by SEQ ID NO: 8, 4, 6, 10, 12, 2 or 14, and more preferably, a polypeptide composed of about 8 to 30 or about 9 to 30 amino acids is sufficient as the polypeptide (a). In some cases, these relatively small polypeptides are presented directly on the surface of the antigen-presenting cell without being incorporated into the antigen-presenting cells.

Further, since a polypeptide incorporated into an antigen-presenting cell is cleaved at random sites by peptidases in the cell to yield various polypeptide fragments, which are then presented on the surface of the antigen-presenting cell, administration of a large polypeptide such as the full-length region of SEQ ID NO: 8, 6, 10, 12, 2 or 14 inevitably causes production of polypeptide fragments by degradation in the antigen-presenting cell, which fragments are effective for immune induction via the antigen-presenting cell. Therefore, also for immune induction via antigen-presenting cells, a large polypeptide can be preferably used, and the polypeptide may be composed of not less than 30, preferably not less than 100, more preferably not less than 200, still more preferably not less than 250 amino acids. The polypeptide may be still more preferably composed of the full-length region of SEQ ID NO: 8, 4, 6, 10, 12, 2 or 14.

The polypeptide described in the (b) above is: a polypeptide, which is obtained by substitution, deletion and/or addition or insertion of a small number of (preferably one or several) amino acid residues in the polypeptide having the amino acid sequence represented by SEQ ID NO: 8, 4, 6, 10, 12, 2 or 14 in the sequence listing and described in the e (a) above, and which has immunity-inducing activity; or a polypeptide, which has a sequence identity of 85% or more, 90% or more, preferably 95% or more, more preferably 98% or more, still more preferably 99% or more, or 99.5% or more with the original (i.e., not modified) sequence, and which has immunity-inducing activity. Generally, it is widely known to those skilled in the art that a protein antigen, even if it has a substitution, deletion, or addition or insertion of a small number of amino acid residues in the amino acid sequence of the protein, may have substantially the same antigenicity as the original protein. Accordingly, a polypeptide defined in the above (b) can exhibit immunity-inducing activity, and thus, can be used in preparation of the immunity-inducing agent of the present invention. It is also preferable that the polypeptide of the above (b) is preferably a polypeptide obtained by substitution, deletion, and/or addition or insertion of one or several amino acid residues in the amino acid sequence represented by SEQ ID NO: 8, 4, 6, 10, 12, 2 or 14. In the specification, the term "several" refers to an integer of 2 to 10, preferably 2 to 6 and further preferably 2 to 4.

As used herein, the term "sequence identity" of amino acid sequences (or nucleotide sequences) means the value calculated by aligning two amino acid sequences (or nucleotide sequences) to be compared such that the number of matched amino acid residues (or nucleotides) is as the largest as possible between the amino acid sequences (or nucleotide sequences), and dividing the number of matched amino acid residues (or the number of matched nucleotides) by the total number of amino acid residues (or the total number of nucleotides), which value is represented as a percentage. When the alignment is carried out, a gap(s) is/are inserted into one or both of the two sequences to be compared as required. Such alignment of sequences can be carried out using a well-known program such as BLAST, FASTA or CLUSTAL W. When a gap(s) is/are inserted, the above-described total number of amino acid residues is the number of residues calculated by counting one gap as one amino acid residue. When the thus counted total number of amino acid residues is different between the two sequences to be compared, the sequence identity (%) is calculated by dividing the number of matched amino acid residues by the total number of amino acid residues in the longer sequence.

The 20 types of amino acids constituting naturally occurring proteins may be classified into groups in each of which similar properties are shared, for example, into neutral amino acids with side chains having low polarity (Gly, Ile, Val, Leu, Ala, Met, Pro), neutral amino acids having hydrophilic side chains (Asn, Gln. Thr, Ser. Tyr, Cys), acidic amino acids (Asp, Glu), basic amino acids (Arg, Lys, His) and aromatic amino acids (Phe, Tyr, Trp). It is known that, in most cases, substitutions of amino acids within the same group do not change the properties of the polypeptide. Therefore, in cases where an amino acid residue(s) in the polypeptide (a) is/are substituted, the probability that the immunity-inducing activity can be maintained becomes high by substitution between amino acids within each group, and so the substitution is preferred.

The polypeptide (c) comprises the polypeptide (a) or (b) as a partial sequence and has an immunity-inducing activity. That is, the polypeptide (c) has at least one other amino acid residue or (one or more) other polypeptide(s) added at one end or both ends of the polypeptide (a) or (b), and has an immunity-inducing activity. Such a polypeptide can also be used in preparation of the immunity-inducing agent of the present invention.

The above-described polypeptides can be synthesized by, for example, a chemical synthesis method such as the Fmoc method (fluorenylmethyloxycarbonyl method) or the tBoc method (t-butyloxycarbonyl method). Further, they can be synthesized by conventional methods using various types of commercially available peptide synthesizers. Further, the polypeptide of interest can be obtained using known genetic engineering techniques, by preparing a polynucleotide encoding the above polypeptide and incorporating the polynucleotide into an expression vector, which is then introduced into a host cell, followed by allowing the polypeptide to be produced in the host cell.

The polynucleotide encoding the above polypeptide can be easily prepared by a known genetic engineering technique or a conventional method using a commercially available nucleic acid synthesizer. For example, DNA having the nucleotide sequence shown in SEQ ID NO: 1 can be prepared by carrying out PCR using a canine chromosomal DNA or cDNA library as a template, and a pair of primers designed such that the nucleotide sequence shown in SEQ NO: 1 can be amplified using the primers. DNA having the nucleotide sequence of SEQ ID NO: 3 can be similarly prepared by using a human chromosomal DNA or cDNA library as the template. The reaction conditions for the PCR can be set appropriately, and examples thereof include, but are not limited to, repeating the reaction process of 94° C. for 30 seconds (denaturation), 55° C. for 30 seconds to 1 minute (annealing) and 72° C. for 2 minutes (extension) as one cycle, for 30 cycles for example, followed by the reaction at 72° C. for 7 minutes. Further, the desired DNA can be isolated by preparing an appropriate probe(s) or primer(s) based on the information of the nucleotide sequences and the amino acid sequences shown in SEQ ID NO: 1 and 3 in Sequence Listing described herein, and screening a cDNA library of dog, human or the like using the probe(s) or primer(s). The cDNA library is preferably prepared from cells, organs or tissues expressing the protein of SEQ ID NO: 2 or 4. The above-described operations such as preparation of a probe(s) or primer(s), construction of a cDNA library, screening of a cDNA library and cloning of a gene of interest are known to those skilled in the art, and can be carried out according to the methods described in Molecular Cloning, Second Edition (Cold Spring Harbor Laboratory Press); Current Protocols in Molecular Biology (JOHN WILLY & SONS); and/or the like. From the thus obtained DNA, DNA encoding the polypeptide (a) can be obtained. Further, since the codons encoding each amino acid are known, the nucleotide sequence of a polynucleotide encoding a specific amino acid sequence can be easily specified. Therefore, since the base sequence of a polynucleotide encoding the polypeptide (b) or polypeptide (c) can also be easily specified, such a polynucleotide can also be easily synthesized using a commercially available nucleic acid synthesizer according to a conventional method.

The host cells are not restricted as long as they can express the above-described polypeptide, and examples thereof include, but are not limited to, prokaryotic cells such as E. coli; and eukaryotic cells such as cultured mammalian cells including monkey kidney cells COS1 and Chinese hamster ovary cells CHO; budding yeast; fission yeast; silkworm cells; and Xenopus laevis egg cells.

When prokaryotic cells are used as the host cells, an expression vector in which an origin that enables replication of the vector in a prokaryotic cell, promoter, Shine-Dalgarno sequence (or ribosome binding site), DNA cloning site, terminator and/or the like is/are contained is used. Examples of the expression vector for E. coli include the pUC system, pBluescript II, pET expression system and pGEX expression system. By incorporating a DNA encoding the above polypeptide into such an expression vector and transforming prokaryotic host cells with the vector, followed by culturing the resulting transformants, the polypeptide encoded by the DNA can be expressed in the prokaryotic host cells. In this process, the polypeptide can also be expressed as a fusion protein with another protein.

When eukaryotic cells are used as the host cells, an expression vector for eukaryotic cells having a promoter, splicing region, poly(A) addition site and/or the like is used as the expression vector. Examples of such an expression vector include pKA1, pCDM8, pSVK3, pMSG, pSVL, pBK-CMV, pBK-RSV, EMI vector, pRS, pcDNA3, pMSG and pYES2. In the same manner as described above, by incorporating a DNA encoding the above polypeptide into such an expression vector and transforming eukaryotic host cells with the vector, followed by culturing the resulting transformants, the polypeptide encoded by the DNA can be expressed in the eukaryotic host cells. In cases where pIND/V5-His, pFLAG-CMV-2, pEGFP-N1, pEGFP-C1 or the like is used as the expression vector, the above polypeptide can be expressed as a fusion protein wherein a tag such as a His tag, FLAG tag, myc tag, HA tag or GFP was added.

For the introduction of the expression vector into the host cells, well-known methods such as electroporation, the calcium phosphate method, the liposome method, and the DEAE dextran method may be used.

Isolation and purification of the polypeptide of interest from the host cells can be carried out by a combination of known separation operations. Examples of the known separation operations include, but are not limited to, treatment with a denaturant such as urea or with a surfactant; sonication treatment; enzyme digestion; salting-out or solvent fractional precipitation; dialysis; centrifugation; ultrafiltration; gel filtration; SDS-PAGE; isoelectric focusing; ion-exchange chromatography; hydrophobic chromatography; affinity chromatography; and reversed-phase chromatography.

The polypeptides obtained by the above method also include, as mentioned above, those in the form of a fusion protein with another arbitrary protein. Examples thereof include fusion proteins with glutathion S-transferase (UST) or with a His tag. Such a polypeptide in the form of a fusion protein also falls within the scope of the present invention as the above-described polypeptide (c). Further, in some cases, a polypeptide expressed in a transformed cell is modified in various ways in the cell after translation. Such a post-translationally modified polypeptide also falls within the scope of the present invention as long as it has an immunity-inducing activity. Examples of such a post-translational modification include: elimination of N-terminal methionine; N-terminal acetylation; glycosylation; limited degradation by an intracellular protease; myristoylation; isoprenylation; and phosphorylation.

2. Immunity-Inducing Agent

As described more specifically in Examples described later; a tumor that has already occurred can be regressed by administration of the polypeptide having an immunity-inducing activity to a tumor-bearing animal. Thus, the immunity-inducing agent of the present invention can be used for treatment and/or prevention of cancers. Further, the polypeptide having an immunity-inducing activity can be used in a method of treating and/or preventing cancers by immunity induction.

As used herein, the terms "tumor" and "cancer" mean a malignant neoplasm, and are used interchangeably.

In this case, the target cancer is preferably a cancer that expresses CSPG5, more preferably, breast cancer, lung cancer, brain tumor, ovarian cancer, leukemia, malignant lymphoma, adenocarcinoma, mastocytoma, squamous cell carcinoma, melanoma, or neuroblastoma, and particularly preferably, breast cancer, lung cancer, brain tumor, leukemia, malignant lymphoma, mastocytoma, melanoma, or neuroblastoma.

The animal of interest (i.e., the subject) is preferably a mammal as described above; more preferably a mammal comprising primate, pet animal, any animal raised in zoo or the like, farm animal, and racing animal; and particularly preferably human, dog, or cat.

The administration route of the immunity-inducing agent of the present invention to a living body may be either oral administration or parenteral administration, and is preferably parenteral administration such as intramuscular administration, subcutaneous administration, intravenous administration or intraarterial administration. When the immunity-inducing agent is used for treatment of cancers, it may be administered to a regional lymph node in the vicinity of the tumor to be treated, as described in the Examples below, in order to enhance its anticancer activity. The dose may be any dose as long as the dose is effective for immunity induction, and, for example, in cases where the agent is used in treatment and/or prevention of cancers, the dose may be one effective for treatment and/or prevention of the cancers. The dose effective for treatment and/or prevention of cancers is appropriately selected depending on the size and symptoms of a tumor and the like, and the effective dose is usually 0.0001 μg to 1000 μg, preferably 0.001 μg to 1000 μg per subject animal per day, which may be administered once or in several times. The agent is preferably administered in several times, every several days to several months. As specifically indicated in the Examples below, the immunity-inducing agent of the present invention can cause regression of a tumor that has already occurred. Therefore, since the agent can exert its anticancer activity also against a small number of cancer cells at an early stage, development or recurrence of cancer can be prevented by using the agent before development of the cancer or after treatment of the cancer. Thus, the immunity-inducing agent of the present invention is effective for both treatment and prevention of cancers.

The immunity-inducing agent of the present invention may consist of the polypeptide(s) alone or may be in the form of a preparation obtained by appropriately admixing additives such as pharmaceutically acceptable carrier, diluent, excipient, and the like, which are suitable for dosage forms. The term "preparation" may be interchangeably used with "a composition for inducing immunity" or "a medicament for inducing immunity". A method for making a preparation, as well as usable additives, is well known in the field of pharmaceutical preparations, and any methods and additives can be used. Examples of the additives include, are not limited to, diluents such as physiological buffer solutions; excipients such as sugar, lactose, cornstarch, calcium phosphate, sorbitol and glycine; binders such as syrup, gelatin, gum Arabic, sorbitol, polyvinyl chloride and tragacanth; and lubricants such as magnesium stearate, polyethylene glycol, talc and silica. Examples of dosage forms may include oral preparations such as tablets, capsules, granules, powder and syrups; and parenteral preparations such as inhalants, injections, suppositories and solutions. These preparations can be produced by methods generally known in the art.

The immunity-inducing agent of the present invention may be used in combination with an immunoenhancer capable of enhancing the immune response in a living body. The immunoenhancer may be contained in the immunity-inducing agent of the present invention or administered as a separate composition to a patient in combination with the immunity-inducing agent of the present invention.

Examples of the immunoenhancer include adjuvants, Adjuvants can enhance the immune response by providing a reservoir of antigen (extracellularly or within macrophages), activating macrophages and stimulating specific sets of lymphocytes, thereby enhancing the immune response and thus the anticancer action. Therefore, especially in cases where the immunity-inducing agent of the present invention is used for treatment and/or prevention of cancers, the immunity-inducing agent preferably comprises an adjuvant, in addition to the above-described polypeptide as an effective ingredient. Many types of adjuvants are well-known in the art, and any of these adjuvants may be used. Specific examples of the adjuvants include MPL (SmithKline Beecham), homologues of *Salmonella minnesota* Re 595 lipopolysaccharide obtained after purification and acid hydrolysis of the lipopolysaccharide; QS21 (SmithKline Beecham), pure QA-21 saponin purified from an extract of *Quillja saponaria*, DQS21 described in PCT application WO96/33739 (SmithKline Beecham); QS-7, QS-17, QS-18 and QS-L1 (So et al., "Molecules and Cells", 1997, Vol. 7, p. 178-186); Freund's incomplete adjuvant; Freund's complete adjuvant; vitamin E; Montanide; Alum or aluminum hydroxide; CpG oligonucleotides (see, for example, Kreig et al., Nature, Vol. 374, p. 546-549); poly-IC and derivatives thereof (e.g., poly ICLC); and various water-in-oil emulsions prepared from biodegradable oils such as squalene and/or tocopherol; and α-galactosylceramide. Among them, the preferred are Freund's incomplete adjuvant, Montanide, poly-IC and derivatives thereof, and CpG oligonucleotides. The mixing ratio between the above-described adjuvant and the polypeptide is typically about 1:10 to 10:1, preferably about 1:5 to 5:1, more preferably about 1:1. However, the adjuvant is not limited to the above-described examples, and adjuvants known in the art other than those described above may also be used when the immunity-inducing agent of the present invention is administered (see, for example, Goding, "Monoclonal Antibodies: Principles and Practice, 2nd edition", 1986). Preparation methods for mixtures or emulsions of a polypeptide and an adjuvant are well-known to those skilled in the art of vaccination.

Further, in addition to the above-described adjuvants, factors that stimulate the immune response of interest may be used as the above-described immunoenhancer. For example, various cytokines having a property to stimulate lymphocytes and/or antigen-presenting cells may be used as the immunoenhancer in combination with the immunity-inducing agent of the present invention. A number of such cytokines capable of enhancing the immune response are known to those skilled in the art, and examples thereof include, but are not limited to, interleukin-12 (IL-12), GM-CSF, IL-18, interferon-α, interferon-β, interferon-ω, interferon-γ, and Flt3 ligand, which have been reported to enhance the prophylactic action of vaccines. Such factors may be used as the immunoenhancer and administered to a patient by adding it to the immunity-inducing agent of the present invention or administered as an independent composition in combination with the immunity-inducing agent of the present invention.

By bringing the above-described polypeptide into contact with antigen-presenting cells (from a subject) ex vivo, in vivo or in vitro, the antigen-presenting cells can be made to present the polypeptide. That is, the polypeptide (a), (b) or (c) described above can be used as the agent for treating antigen-presenting cells. Examples of the antigen-presenting cells which may be preferably used include dendritic cells or B cells having an MHC class I molecule. Various MHC class I molecules have been identified and are well-known. MHC molecules in human are called HLA. Examples of HLA class I molecules include HLA-A, HLA-B and HLA-C, more specifically, HLA-A1, HLA-A0201, HLA-A0204, HLA-A0205, HLA-A0206, HLA-A0207, HLA-A11, HLA-A24, HLA-A31, HLA-A6801, HLA-B7, HLA-B8, HLA-B2705, HLA-B37, HLA-Cw0401 and HLA-Cw0602.

Examples of the use of the above-described polypeptide in treatment of antigen-presenting cells, as described in Section 3 below, include using the polypeptide for preparing an antigen-presenting cell containing a complex of the polypeptide and an MHC molecule, and using the polypeptide for preparing a cytotoxic T cell specific to the polypeptide.

The dendritic cells or B cells having an MHC class I molecule can be prepared from peripheral blood by a well-known method. For example, tumor-specific dendritic cells can be induced by inducing dendritic cells from bone marrow, umbilical cord blood or patient's peripheral blood using granulocyte-macrophage colony-stimulating factor (GM-CSF) and IL-3 (or IL-4), and then adding a tumor-associated peptide to the culture system.

By administering an effective amount of such dendritic cells, a response desired for therapy of a cancer can be induced. As the cells to be used, bone marrow or umbilical cord blood donated by a healthy individual, or bone marrow, peripheral blood or the like from the patient himself may be used. When autologous cells of the patient are used, high safety can be attained and serious side effects are expected to be avoided. The peripheral blood or bone marrow may be any of fresh sample, cold-stored sample and frozen sample.

As for the peripheral blood, whole blood may be cultured or the leukocyte components alone may be separated and cultured, and the latter is more efficient and thus preferred. Further, among the leukocyte components, mononuclear cells may be separated. In cases where the cells are originated from bone marrow or umbilical cord blood, the whole cells constituting the bone marrow may be cultured, or mononuclear cells may be separated therefrom and cultured. Peripheral blood, the leukocyte components thereof and bone marrow cells contain mononuclear hematopoietic stem cells and immature dendritic cells, from which dendritic cells are originated, and also CD4-positive cells and the like. As for the cytokine to be used, the production method thereof is not restricted, and a naturally-occurring or recombinant cytokine or the like may be employed as long as its safety and physiological activity have been confirmed. Preferably, a preparation with assured quality for medical use is used in a minimum necessary amount. The concentration of the cytokine(s) to be added is not restricted as long as the dendritic cells are induced at the concentration, and usually, the total concentration of the cytokine(s) is preferably about 10-1000 ng/mL, more preferably about 20-500 ng/mL. The cultivation may be carried out using a well-known medium usually used for cultivation of leukocytes. The culturing temperature is not restricted as long as proliferation of the leukocytes is attained at the temperature, and a temperature of about 37° C., which is the body temperature of human, is most preferred. The atmospheric environment during the culturing is not restricted as long as proliferation of the leukocytes is attained under the environment, and 5% $CO_2$ is preferably ventilated. The culturing period is not restricted as long as a necessary number of the cells are induced during such period, being usually 3 days to 2 weeks. As for the apparatuses used for separation and cultivation of the cells, appropriate apparatuses, preferably those whose safety upon application to medical uses have been confirmed and whose operations are stable and simple, may be employed, in particular, as for the cell-culturing apparatus, not only a general vessel such as Petri dish, flask or bottle, but also a layer type vessel, multistage vessel, roller bottle, spinner type bottle, bag type culturing vessel, hollow fiber column or the like may be used.

Also by expressing a polynucleotide encoding the polypeptides (a), (b) or (c) in the body of a subject animal, antibody production and cytotoxic cells can be induced in the living body, and an effect comparable to that obtained in the case of administration of the polypeptide can be obtained. That is, the immunity-inducing agent of the present invention may be one comprising, as an effective ingredient, a recombinant vector having a polynucleotide encoding the polynucleotide (a), (b) or (c), which recombinant vector is capable of expressing the polypeptide in a living body. Such a recombinant vector capable of expressing an antigenic polypeptide as shown in Examples described below is also called a gene vaccine.

The vector used for production of the gene vaccine is not restricted as long as it is a vector capable of expressing the polypeptide in a cell of a subject animal (preferably in a mammalian cell), and may be either a plasmid vector or a virus vector, and any vector known in the field of gene vaccines may be used. The polynucleotide such as DNA or RNA encoding the above-described polypeptide can be easily prepared as mentioned above by a conventional method. Incorporation of the polynucleotide into the vector can be carried out using a method well-known to those skilled in the art.

The administration route of the gene vaccine is preferably a parenteral route such as intramuscular, subcutaneous, intravenous or intraarterial administration, and the dose may be appropriately selected depending on the type of the antigen and the like, and is usually about 0.1 µg to 100 mg, preferably about 1 µg to 10 mg in terms of the weight of the gene vaccine per 1 kg of body weight.

Examples of the method using a virus vector include those wherein a polynucleotide encoding the above-described polypeptide is incorporated into an RNA virus or DNA virus, such as a retrovirus, adenovirus, adeno-associated virus, herpes virus, vaccinia virus, pox virus, poliovirus or Sindbis virus, and then a subject animal is infected with the resulting virus. Among these methods, those using a retrovirus, adenovirus, adeno-associated virus, vaccinia virus or the like are especially preferred.

Examples of other methods include a method wherein an expression plasmid is directly intramuscularly administered (DNA vaccine method), a liposome method, a lipofectin method, a microinjection method, a calcium phosphate method and an electroporation method, and the DNA vaccine method and the liposome method are especially preferred.

Methods for actually allowing a gene encoding the above-described polypeptide used in the present invention to act as a drug include an in vivo method wherein the gene is directly introduced into the body, and an ex vivo method wherein a certain kind of cells are collected from a subject animal and the gene is introduced into the cells outside the body, followed by returning the cells to the body (Nikkei Science, 1994, April, p. 20-45; The Pharmaceutical Monthly, 1994, Vol. 36, No. 1, p. 23-48; Experimental Medicine, Extra Edition, 1994, Vol. 12, No. 15; and references cited in these literatures, and the like). The in vivo method is more preferred.

When the gene is administered by the in vivo method, it may be administered through an appropriate administration route depending on a disease to be treated, symptom and so on. The gene may be administered by, for example, intravenous; intraarterial, subcutaneous or intramuscular administration. When the gene is administered by the in vivo method, it may be formulated into a preparation such as a solution, and in general, it is formulated into an injection solution or the like containing DNA encoding the above-described peptide of the present invention as an effective ingredient, and where needed, a pharmaceutically acceptable carrier (e.g., physiological saline or buffer solution) may be further added to the solution. In the case of a liposome or membrane fusion liposome e.g., Sendai virus (HVJ)-liposome) containing the DNA, the liposome may be formulated into a liposome preparation such as a suspension, a frozen preparation, or a centrifugally concentrated frozen preparation.

In the present invention, "the nucleotide sequence represented by SEQ ID NO:1" includes not only the nucleotide sequence represented by SEQ ID NO:1 itself, but also the sequence complementary thereto. Thus, "the polynucleotide having the nucleotide sequence represented by SEQ ID NO:1" includes a single-stranded polynucleotide having the nucleotide sequence represented by SEQ ID NO:1 itself, a single-stranded polynucleotide having the nucleotide sequence complementary thereto, and a double-stranded polynucleotide composed of these single-stranded polynucleotides. When a polynucleotide encoding a polypeptide used in the present invention is prepared, any one of these nucleotide sequences is appropriately selected, and those skilled in the art can easily carry out the selection.

3. Antigen-Presenting Cell or Cytotoxic T Cell

The present invention further provides a method for preparing an antigen-presenting cell containing a complex of the polypeptide as mentioned above and an MHC molecule, comprising contacting the polypeptide with an antigen-presenting cell from a subject ex vivo or in vitro.

The present invention also provides an antigen-presenting cell characterized by containing a complex of the polypeptide as mentioned above and an MHC molecule and obtained by the method.

The method itself of contacting the polypeptide as mentioned above with an antigen-presenting cell ex vivo or in vitro, can be carried out by a method well known in the art, for example, by culturing the antigen-presenting cell in a culture liquid containing the polypeptide. As the medium, commercially available media for culturing antigen-presenting cells can be used. The concentration of the peptide in the medium, which is not particularly limited, is usually about 1 to 100 µg/ml and preferably about 5 to 20 µg/ml. The cell density during culturing, which is not particularly limited, is usually about $10^3$ to $10^7$ cells/ml and preferably about $5 \times 10^4$ to $5 \times 10^6$ cells/ml. The culture is preferably carried out by routine methods at 37° C. in 5% $CO_2$ atmosphere. The length of a peptide that can be presented by the antigen-presenting cell on the surface thereof is usually about 30 amino acid residues at a maximum. Accordingly, when the antigen-presenting cell is contacted with the polypeptide ex vivo or in vitro, the polypeptide may be prepared so as to have a length of 30 amino acid residues or less; however, the length is not limited to this.

By culturing the antigen-presenting cell in the presence of the polypeptide as mentioned above, the polypeptide is integrated into an MHC molecule of the antigen-presenting cell and presented on the surface of the antigen-presenting cell. Accordingly, it is possible to prepare an isolated antigen-presenting cell containing a complex of the polypeptide and the MHC molecule. Such an antigen-presenting cell can present the polypeptide in vivo, ex vivo or in vitro to a T cell and can induce and deposit a cytotoxic T cell specific to the polypeptide.

The present invention further provides a method for preparing a cytotoxic T cell specific to the polypeptide as mentioned above, comprising contacting the antigen-presenting cell with a T cell from a subject ex vivo or in vitro to activate the T cell.

The present invention also provides a cytotoxic T cell specific to the polypeptide as mentioned above, obtained by this method.

By contacting an antigen-presenting cell, which contains a complex of the polypeptide as mentioned above and an WIC molecule, prepared in the above-mentioned manner with a T cell ex vivo or in vitro, the cytotoxic T cell specific to the polypeptide can be induced and proliferated. The contact can be made by co-culturing the antigen-presenting cell and the T cell in a liquid medium; for example, by suspending the antigen-presenting cell in a liquid medium, placing the resultant suspension in a container such as wells of a micro plate, adding the T cell to the wells, and culturing them. The mixing ratio of the antigen-presenting cell and the T cell during the co-culture, which is not particularly limited, is usually, about 1:1 to about 1:100, preferably about 1:5 to about 1:20 in terms of a ratio of the numbers of the cells. The density of the antigen-presenting cell in the liquid medium, which is not particularly limited, is usually, about 100 to 10,000,000 cells/ml and preferably about 10,000 to 1,000,000 cells/ml. The co-culture is preferably carried out by routine methods at 37° C. in 5% $CO_2$ atmosphere. As the medium, a commercially available culture medium for antigen-presenting cell/T cell can be used. The culture time, which is not particularly limited, is usually, about 2 days to 3 weeks and preferably about 4 days to 2 weeks. The co-culture is preferably carried out in the presence of one or more types of interleukins such as IL-2, IL-6, IL-7 and IL-12. In this case, the concentrations of IL-2 and IL-7 are usually about 5 to 20 U/ml, the concentration of IL-6 is usually about 500 to 2000 U/ml, and the concentration of IL-12 is usually about 5 to 20 ng/ml; however, the concentrations are not limited to these. The co-culture may be repeated once or several times by supplementing the fresh antigen-presenting cell. For example, an operation, which comprises discarding the culture supernatant after co-culture, adding a suspension of the fresh antigen-presenting cell, and carrying out co-culture, may be repeated once or several times. The co-culturing conditions may be the same as above.

Through the co-culture, the cytotoxic T cell specific to the polypeptide is induced and proliferated. Accordingly, using the above-mentioned polypeptide can use to prepare an isolated T cell that selectively binds a complex of the polypeptide and the MEW molecule.

As described in Examples below, the CSPG5 gene is specifically expressed in a breast cancer cell, a breast cancer tissue, a lung cancer cell, a lung cancer tissue, a liver cancer cell, a liver cancer tissue, a brain tumor cell, a brain tumor tissue, an ovary cancer cell, an ovary cancer tissue, leukemia, malignant lymphoma, an adenocarcinoma cell, an adenocarcinoma tissue, mastocytoma, a squamous cell carcinoma cell, a melanoma cell, or a neuroblastoma cell. Accordingly, in these cancers, it is thought that CSPG5 is significantly more largely present than in normal cells. If the cytotoxic T cell prepared in the above-described manner is administered in vivo such that a part of the CSPG5 polypeptide existing in cancer cells is presented by the MEW molecule on the surface of a cancer cell, the cytotoxic T cell can damage the cancer cell by using the part of the CSPG5 polypeptide as a marker. The antigen-presenting cell presenting a part of the CSPG5 polypeptide can induce and proliferate the cytotoxic T cell specific to the polypeptide in vivo. Thus, cancer cells can also be damaged by administering the antigen-presenting cell to a living body. More specifically, the cytotoxic T cell and the antigen-presenting cell prepared by use of the above-mentioned polypeptide are also useful for treating and/or preventing cancer similarly to the immunity-inducing agent of the present invention.

In cases where the above-described isolated antigen-presenting cells or isolated T cells are administered to a living body, these are preferably prepared by treating antigen presenting cells or T cells collected from the patient to be treated with the polypeptide (a), (b) or (c) as described above in order to avoid the immune response in the living body that attacks these cells as foreign bodies.

The treating and/or preventing agent for cancer comprising, as an effective ingredient, the antigen-presenting cells or T cells is preferably administered via a parenteral administration route, for example, by intravenous or intraarterial administration. The dose is appropriately selected depending on the symptoms, the purpose of administration and the like, and is usually 1 cell to 10,000,000,000,000 cells, preferably 1,000,000 cells to 1,000,000,000 cells, which dose is preferably administered once every several days to once every several months. The preparation may be, for example, the cells suspended in physiological buffered saline, and the preparation may be used in combination with another anticancer agent(s), cytokine(s) or the like. Further, one or more additives well-known in the field of pharmaceuticals may also be added.

EXAMPLES

Now, the present invention will be more specifically described below based on Examples; however, the scope of the present invention is not limited by Examples.

Example 1

<Obtaining Novel Cancer Antigen Protein by SEREX Method>

(1) Preparation of cDNA Library

Total RNA was extracted from canine testes in accordance with the Acid guanidium-Phenol-Chloroform method, and then, poly(A) RNA was purified by using Oligotex-dT30 mRNA purification Kit (Takara Shuzo Co., Ltd., Kyoto, Japan) in accordance with the protocol attached to the kit.

Using the obtained mRNA (5 µg), a cDNA phage library was synthesized. For the preparation of the cDNA phage library, cDNA Synthesis kit, Zap-cDNA Synthesis Kit or ZAP-cDNA GigapackIII Gold Cloning Kit (STRATA-GENE) were used in accordance with the protocol attached to the kit. The size of the prepared cDNA phage library was $1 \times 10^6$ pfU/ml.

(2) Screening of cDNA Library with Serum

Using the prepared cDNA phage library, immunoscreening was carried out. More specifically, host *E. coli* (XL1-Blue MRF') was infected with the phage so as to obtain 2340 clones in an NZY agarose plate of φ90×15 mm and cultured at 42° C. for 3-4 hours to obtain plaques. The plate was covered with nitrocellulose membrane (Hybond C Extra: GE Healthcare Bio-Science) impregnated with IPTG (isopropyl-β-D-thiogalactoside) at 37° C. for 4 hours to induce protein expression and the protein was transferred to the membrane. Thereafter, the membrane was taken, soaked in TBS (10 mM Tris-HCl, 150 mM NaCl pH7.5) containing 0.5% of skim milk powder, and shaken at 4° C. overnight to suppress a nonspecific reaction. This filter was allowed to react with the 500-fold diluted serum of a disease dog at room temperature for 2 to 3 hours.

As the disease-dog sera mentioned above, the sera taken from breast cancer dogs were used. The sera were stored at −80° C. and pretreated immediately before use. The method of the pretreatment of the sera was as follows. That is, first, the host *Escherichia coli* (XL1-Blure MRF') was infected with λ ZAP Express phage into which no foreign gene was inserted, and then cultured on a NZY plate medium at 37° C. overnight. Subsequently, 0.2 M NaHCO$_3$ buffer (pH8.3) containing 0.5 M NaCl was added to the plate, and the plate was left to stand at 4° C. for 15 hours, followed by collecting the supernatant as an *Escherichia coli*/phage extract. Thereafter, the collected *Escherichia coli*/phage extract was allowed to flow through a NHS-column (GE Healthcare Bio-Science) to immobilize proteins derived from *Escherichia coli*/phage onto the column. The serum from the canine patient was allowed to flow through and to react with the protein-immobilized column to remove antibodies adsorbed to *Escherichia coli* and phage from the serum. The serum fraction passed though the column was diluted 500 fold with TBS containing 0.5% of skim milk powder, and the resulting diluent was used as a material for immunoscreening.

The membrane on which the thus treated serum and the above-described fusion protein were blotted was washed 4 times with TBS-T (0.05% Tween 20/TBS), and allowed to react with goat anti-dog IgG (Goat anti Dog IgG-h+1 HRP conjugated; BETHYL Laboratories) 5.000-fold diluted with IBS containing 0.5% skim milk powder as a secondary antibody at room temperature for 1 hour, followed by detection by the enzyme coloring reaction using the NBT/BCIP reaction solution (Roche). Colonies at positions where a positive coloring reaction was observed were recovered from the NZY agarose plate having a size of Φ90×15 mm, and dissolved in 500 µl of SM buffer (100 mM NaCl, 10 mM MgClSO$_4$, 50 mM Tris-HCl, 0.01% gelatin; pH 7.5). The screening was repeated as a second and third screening in the same manner as described above until a single coloring reaction-positive colony was obtained, thereby isolating one positive clone after screening of 9110 phage clones reactive with IgG in the serum.

(3) Sequence-Identity Search of Isolated Antigen Gene

In order to subject the single positive clone isolated by the above-described method to nucleotide sequence analysis, an operation for conversion of the phage vector to a plasmid vector was carried out. Specifically, a solution (200 µL) containing host *Escherichia coli* (XL1-Blue MRF') prepared so as to show an absorbance OD$_{600}$ of 1.0, a purified phage solution (100 µL), and further 1 µL of ExAssist helper phage (STRATAGENE) were mixed and allowed to react at 37° C. for 15 minutes. LB medium (3 mL) was added and cultivation was carried out at 37° C. for 2.5-3 hours. The resulting culture was immediately kept in a water bath at 70° C. for 20 minutes, and then was centrifuged at 4° C. at 1000×g for 15 minutes to recover the supernatant as a phargemid solution. Subsequently, a solution (200 µL) containing a phargemid host *Escherichia coli* (SOLR) prepared so as to have an absorbance OD$_{600}$ of 1.0 and the purified phage solution (10 µL) were mixed and allowed to react at 37° C. for 15 minutes. The resultant solution (50 µL) was seeded on an ampicillin (final concentration: 50 µg/mL)-containing LB agar medium and cultured at 37° C. overnight. A single transformed SOLR colony was picked up, cultured in ampicillin (final concentration: 50 µg/mL)-containing LB medium at 37° C. and, thereafter, purified by QIAGEN plasmid Miniprep Kit (QIAGEN) to obtain a plasmid DNA having a desired insert.

The purified plasmid was subjected to the primer walking using T3 primer represented by SEQ ID NO: 17 and T7 primer represented by SEQ ID NO: 18 to analyze the full-length sequence of the insert. The gene sequence represented by SEQ ID NO: 1 was obtained by the sequencing analysis. Using the nucleotide sequence of the gene and amino acid sequence therefor, the sequence identity search, which is a search for identical sequence with known genes, was carried out by the sequence identity search program BLAST search (http://www.ncbi.nlm.nih.gov/BLAST/). As a result, it was found that the gene obtained above is CSPG5 gene. In the human CSPG5, which is a human factor homologous with canine CSPG5, the nucleotide-sequence identity and the amino acid sequence identity with the canine CSPG5 were both 87%. In cat CSPG5, the nucleotide sequence identity was 92% and the amino acid sequence identity was 91%. In mouse homologous factor, i.e., mouse CSPG5, the nucleotide sequence identity was 84% and the amino acid sequence identity was 85%. The nucleotide sequences of the human CSPG5 are represented by SEQ ID NOs: 3, 5, 7, 9 and 11 and the amino acid sequences thereof are represented by SEQ ID NO: 4, 6, 8, 10 and 12. The nucleotide sequence of the cat CSPG5 is represented by SEQ ID NO: 13 and the amino acid sequence therefor is represented by SEQ ID NO: 14. The nucleotide sequence of the mouse CSPG5 is represented by SEQ ID NO: 15 and the amino acid sequence thereof is represented by SEQ ID NO: 16.

(4) Gene Expression Analysis in Different Tissues

Figure 2:
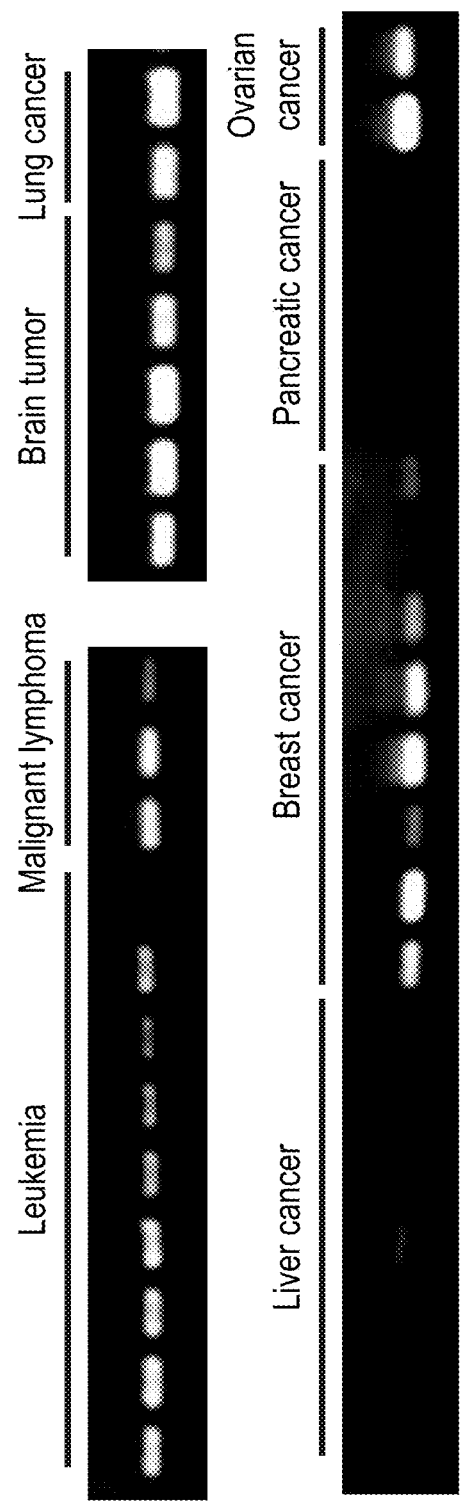
FIG. 2 This figure shows expression patterns of CSPG5 gene identified in human tumor tissues or cancer cell lines. Human GAPDH gene was found to be expressed in all of the human tissues and cell lines.
Figure 3:
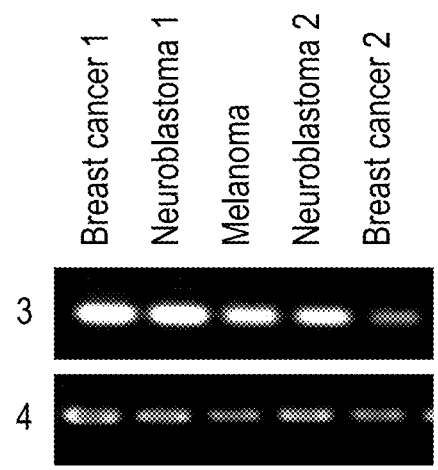
FIG. 3 This figure shows expression patterns of CSPG5 gene identified in mouse tumor tissues or cancer cell lines. Reference number 3 shows expression patterns of the mouse CSPG5 gene in individual mouse tissues and cell lines; reference number 4 shows expression patterns of mouse GAPDH gene in individual mouse tissues and cell lines.

Expression of the genes obtained by the above method in normal tissues and cancer tissues and cancel cell lines from dogs, humans and mice was examined by a RT-PCR (Reverse Transcription-PCR) method. The reverse transcription reaction was carried out as follows. First, total RNAs were extracted from individual tissues (50-100 mg) and individual cell lines (5-10×10$^6$ cells) by use of TRIZOL reagent (Invitrogen) in accordance with the protocol attached. Using the total RNAs, cDNAs were synthesized by using Superscript First-Strand Synthesis System for RT-PCR (Invitrogen) in accordance with the protocol attached. As the cDNAs of the human normal tissues (from the brain, hippocampus, testis, colon, and placenta), gene pool cDNA (Invitrogen), QUICK-Clone cDNA (Clontech) and Large-Insert cDNA Library (Clontech) were used. The PCR reaction was carried out by using the gene specific primers obtained (canine primers are represented by SEQ ID NOs: 19 and 20, human primers are represented by SEQ ID NOs: 21 and 22, mouse primers are represented by SEQ ID NOs: 23 and 24), as follows. That is, reagents were added to the attached buffer wherein the reagents hat it contain 0.25 μL of the sample prepared by the reverse transcription reaction, the above primers (2 μM for each), dNTPs (0.2 mM for each) and a 0.65 U ExTaq polymerase (Takara Shuzo Co., Ltd.). The reaction mixture 25 μl, in total was subjected to PCR using a Thermal Cycler (BIO RAD). In the PCR, 30 cycles were repeated wherein one cycle consists of the treatments: at 94° C. for 30 seconds; 55° C. for 30 seconds; and at 72° C. for one minute. For comparison, GAPDH-specific primers (i.e., canine and human GAPDH primers represented by SEQ ID NOs: 25 and 26, and mouse GAPDH primers represented by SEQ ID NOs: 27 and 28) were simultaneously used. As a result, as shown in FIG. 1, the canine CSPG5 gene was not expressed in almost all normal canine tissues, but it was strongly expressed in the canine tumor tissues. Similarly to the canine CSPG5 gene, the expression of human and mouse CSPG5 genes in normal human and mouse tissues was almost not confirmed; however, the expression thereof was detected in cancer cells, i.e. breast cancer, lung cancer, brain tumor, ovarian cancer, leukemia, malignant lymphoma cell lines (FIGS. 2 and 3).

Example 2

<Analysis for In Vivo Cancer Antigenicity of CSPG5>

(1) Preparation of Recombinant Vector Expressing CSPG5 In Vivo

A recombinant vector expressing CSPG5 in vivo was prepared based on the nucleotide sequence represented by SEQ ID NO: 15 in accordance with the following method. PCR was carried out as follows. A reaction mixture was prepared by adding reagents: a cDNA molecule (1 μL), which was prepared from mouse neuroblastoma cell line 1 (N2a: purchased from ATCC) whose expression was observed in Example 1, two types of primers (0.4 μM for each) having HindIII and XbaI restriction enzyme cleaved sequences (represented by SEQ ID NOs: 29 and 30), 0.2 mM dNTPs, and 1.25 U PrimeSTAR HS polymerase (Takara Shuzo Co., Ltd.), and the buffer attached so as to obtain a total amount of 50 μL; and subjected to PCR using a Thermal Cycler (BIO RAD). In the PCR, 30 cycles were repeated wherein one cycle consists of the treatments: at 98° C. for 10 seconds; at 55° C. for 15 seconds; and at 72° C. for 4 minutes. The above-mentioned two types of primers were used for amplifying a region encoding a full-length amino acid sequence represented by SEQ ID NO: 15. After the PCR, the amplified DNA was electrophoresed on 1% agarose gel, and a DNA fragment of appropriately 1000 bp was purified by use of QIAquick Gel Extraction Kit (QIAGEN).

The purified DNA fragment was ligated to the cloning vector pCR-Blunt (Invitrogen), which vector was then transformed into E. coli cells, followed by recovering the plasmid vector. By its sequencing, it was confirmed that the sequence of the amplified gene fragment was identical with a desired sequence. The plasmid whose sequence was identical with the desired sequence was treated with HindIII and XbaI restriction enzymes. After purification was carried out with QIAquick Gel Extraction Kit, a desired gene sequence was inserted into the mammalian expression vector PCDNA3.1 (Invitrogen) treated with HindIII and XbaI restriction enzymes. Owing to the use of the vector, CSPG5 protein is produced in a mammalian cell.

To plasmid DNA (100 μg) prepared above, 50 μg of gold particles (Bio Rad), spermidine (100 μl) (SIGMA) and 1M CaCl$_2$) (100 μl (SIGMA)) were added. The mixture was stirred by a vortex and allowed to stand for 10 minutes at room temperature (hereinafter referred to as "gold-DNA particles"). After centrifugation at 3000 rpm for one minute, the supernatant was discarded, followed by washing the pellet three times with 100% ethanol (WAKO). To the gold-DNA particles, 100% ethanol (6 ml) was added, and the mixture was stirred sufficiently by a vortex. The gold-DNA particles were poured in Tefzel Tubing (Bio Rad) to precipitate them on its wall. The Tefzel Tubing with attached gold-DNA particles was dried in the air by removing ethanol and thereafter cut into pieces having a length suitable for use in gene gun.

(2) Antitumor Effect of CSPG5 by DNA Vaccine Method

Ten A/J mice (7 weeks old, male, purchased from Japan SLC) were used. The tube prepared above was immobilized on a gene gun. A DNA vaccine was percutaneously administered to the shaved peritoneal cavity of mice with the help of pure helium gas at a pressure of 400 psi three times every 7 days (plasmid DNA inoculation amount: 2 μg/animal). After the percutaneous administration, the N2a cells, which are a mouse neuroblastoma cell line, were grafted to each mouse to evaluate the antitumor effect (referred to as a prevention model). For the control, the plasmid DNA without inserted CSPG5 gene was administered to 10 mice in each model group.

The antitumor effect was evaluated for the size of a tumor (long diameter×(short diameter)$^2$/2) and the rate of surviving mice. As the result, in the prevention model, the tumor sizes after 21 days of the control group and the CSPG5 plasmid administration group were 1866 mm$^3$ and 459 mm$^3$, respectively. Thus, it was found that the tumor size was significantly reduced in the CSPG5 plasmid administration group. As the result that the survival situation was observed in the prevention model, the whole cases of the control group died 54 days after administration; whereas in the CSPG5 plasmid administration group, 60% of the mice were alive. From these results, the significant antitumor effect on the CSPG5 plasmid administration group compared to the control group was demonstrated.

INDUSTRIAL APPLICABILITY

The present invention provides an immunity-inducing agent comprising a polypeptide exhibiting an antitumor activity to cancers and thus is useful for treating and/or preventing cancers.

SEQUENCE LISTING FREE TEXT

SEQ ID NO: 17: T3 primer
SEQ ID NO: 18: T7 primer
SEQ ID NO: 19: Canis (dog) RT primer sense
SEQ ID NO: 20: Canis (dog) RT primer antisense
SEQ ID NO: 21: human RT primer sense
SEQ ID NO: 22: human RT primer anti sense
SEQ ID NO: 23: mouse RT primer sense
SEQ ID NO: 24: mouse RT primer antisense
SEQ ID NOs: 25 and 26: GAPDH primer
SEQ ID NOs: 27 and 28: GAPDH primer
SEQ ID NO: 29: mus-fullCSPG5 primer sense
SEQ ID NO: 30: mus-fullCSPG5 primer antisense All publications, patents and patent applications cited herein are incorporated by reference in their entirety.

The invention claimed is:

1. A method of inducing an immune response in a cancer patient, said method comprising administering an effective amount of an immunity-inducing agent to said cancer patient;
wherein said immunity-inducing agent comprises, as an active ingredient, at least one polypeptide having immunity-inducing activity and selected from:
a polypeptide comprising or consisting of the amino acid sequence of SEQ ID NO: 8, 4, or 10;
wherein the cancer is a CSPG5 expressing cancer.

2. The method of inducing immunity according to claim 1, wherein the polypeptide having immunity-inducing activity is a polypeptide consisting of the amino acid sequence of SEQ ID NO: 8, 4, or 10.

3. The method of inducing immunity according to claim 1, further comprising administering an immunoenhancer to said cancer patient.

4. The method of inducing immunity according to claim 3, wherein the immunoenhancer is at least one selected from the group consisting of a Freund's incomplete adjuvant, Montanide, Poly IC and derivatives thereof, CpG oligonucleotides, interleukin 12, interleukin 18, interferon α, interferon β, interferon ω, interferon γ, and a Flt 3 ligand.

5. A method of treating cancer, said method comprising administering a pharmaceutical composition comprising an immunity-inducing agent and a pharmaceutically acceptable carrier to a subject in need thereof;
wherein said immunity-inducing agent comprises, as an active ingredient, at least one polypeptide having immunity-inducing activity and selected from
a polypeptide comprising or consisting of the amino acid sequence of SEQ ID NO: 8, 4, or 10;
wherein the cancer is a CSPG5 expressing cancer.

6. The method of treatment according to claim 5, wherein the polypeptide having immunity-inducing activity is a polypeptide consisting of the amino acid sequence of SEQ ID NO: 8, 4, or 10.

7. The method of treatment according to claim 5, wherein the cancer is brain tumor, leukemia, malignant lymphoma, or neuroblastoma.

8. The method of treatment according to claim 5, wherein said pharmaceutical composition comprises an immunoenhancer.

9. The method of treatment according to claim 8, wherein the immunoenhancer is at least one selected from the group consisting of a Freund's incomplete adjuvant, Montanide, Poly IC and derivatives thereof, CpG oligonucleotides, interleukin 12, interleukin 18, interferon α, interferon β, interferon ω, interferon γ, and a Flt 3 ligand.

10. The method of treatment according to claim 5, wherein the cancer is a brain tumor;
wherein the polypeptide having immunity-inducing activity is SEQ ID NO: 8; and
wherein the pharmaceutical composition comprises an immunoenhancer of Poly IC or a derivative thereof.

* * * * *

```
                        SEQUENCE LISTING

<160> NUMBER OF SEQ ID NOS: 30

<210> SEQ ID NO 1
<211> LENGTH: 2270
<212> TYPE: DNA
<213> ORGANISM: Canis familiaris
<220> FEATURE:
<221> NAME/KEY: CDS
<222> LOCATION: (1)..(1434)
<223> OTHER INFORMATION:

<400> SEQUENCE: 1 ggg gag gag gag acc tcg tgt act gca cct ggc ggc ctg ccg gcc gtg      48
Gly Glu Glu Glu Thr Ser Cys Thr Ala Pro Gly Gly Leu Pro Ala Val
1               5                   10                  15 gtg ggg cct ggg gtc ggg cca gag gag gcg ctg gag gcg tcc gcg gcc      96
Val Gly Pro Gly Val Gly Pro Glu Glu Ala Leu Glu Ala Ser Ala Ala
            20                  25                  30 gtg acc ggc aca gcc tgg ctg gag gct gac agc ccg ggc ctg ggc gga     144
Val Thr Gly Thr Ala Trp Leu Glu Ala Asp Ser Pro Gly Leu Gly Gly
        35                  40                  45 gcg acc gta gag gct ggc agc ggc gac acc cag gcc ctt ccg gcc acg     192
Ala Thr Val Glu Ala Gly Ser Gly Asp Thr Gln Ala Leu Pro Ala Thr
    50                  55                  60 ctc ccg act ccg gag gag gcc ctc cga cgt gca tcg gtg gcc ccc gcc     240
Leu Pro Thr Pro Glu Glu Ala Leu Arg Arg Ala Ser Val Ala Pro Ala
65                  70                  75                  80 acc ccc gag act aca gag gcc agc gga cca ccc tcc ccc act cct ggc     288
Thr Pro Glu Thr Thr Glu Ala Ser Gly Pro Pro Ser Pro Thr Pro Gly
                85                  90                  95 gac cag cta cgc cca ggc ccc gaa ctc ccc aag gag agc ccc ttg gag     336
Asp Gln Leu Arg Pro Gly Pro Glu Leu Pro Lys Glu Ser Pro Leu Glu
            100                 105                 110 gtt tgg ctg aac ctg gga ggc agc aca cat gac ccg cat ggg cca gag     384
Val Trp Leu Asn Leu Gly Gly Ser Thr His Asp Pro His Gly Pro Glu
        115                 120                 125 ccc acg ttc ccc ttt cag ggc aca ctg gag ccc cgg ccg gcg tca gat     432
Pro Thr Phe Pro Phe Gln Gly Thr Leu Glu Pro Arg Pro Ala Ser Asp
    130                 135                 140 atc att gac atc gac tac ttc gaa gga ttg gat ggt gag ggc cgt ggc     480
Ile Ile Asp Ile Asp Tyr Phe Glu Gly Leu Asp Gly Glu Gly Arg Gly
145                 150                 155                 160 gcc gac ttg ggg agc ttc ccg gtg tcg cca gga acc tca gag cac cac     528
Ala Asp Leu Gly Ser Phe Pro Val Ser Pro Gly Thr Ser Glu His His
                165                 170                 175 ccc gat act ggg gga gag acc cct tcc tgg agc ctg ctt gac tta tac     576
Pro Asp Thr Gly Gly Glu Thr Pro Ser Trp Ser Leu Leu Asp Leu Tyr
            180                 185                 190 gat gac ttc acc ccc ttt gat gaa tct gac ttc tac ccc act aca tcc     624
```

```
Asp Asp Phe Thr Pro Phe Asp Glu Ser Asp Phe Tyr Pro Thr Thr Ser
        195                 200                 205 ttc tat gat gac ttg gag gaa gag gag gag gaa gag gat gac gac aag      672
Phe Tyr Asp Asp Leu Glu Glu Glu Glu Glu Glu Glu Asp Asp Asp Lys
210                 215                 220 gat gca gcg gaa ggt gga gac ctg gaa gat gaa agt gac ctt ctg gtg      720
Asp Ala Ala Glu Gly Gly Asp Leu Glu Asp Glu Ser Asp Leu Leu Val
225                 230                 235                 240 ccc act gag aag cct ggg ctg agg cca ggg cct ggc cag ccc acc agt      768
Pro Thr Glu Lys Pro Gly Leu Arg Pro Gly Pro Gly Gln Pro Thr Ser
                245                 250                 255 cgg tgg cat gct gtc ccc cca cag cat act ctg ggg ttg gtc cct ggc      816
Arg Trp His Ala Val Pro Pro Gln His Thr Leu Gly Leu Val Pro Gly
            260                 265                 270 agc agc atc gcc ctc aga ccc cgt ccg gga gag ccg ggc agg gac ctg      864
Ser Ser Ile Ala Leu Arg Pro Arg Pro Gly Glu Pro Gly Arg Asp Leu
        275                 280                 285 gcc ccg agc gag aac ggc act gag tgc cgc agc ggc ttt gtg cgg cat      912
Ala Pro Ser Glu Asn Gly Thr Glu Cys Arg Ser Gly Phe Val Arg His
290                 295                 300 aac ggc tcc tgc cga tcc gtg tgc gac ctc ttc cca agt tac tgt cac      960
Asn Gly Ser Cys Arg Ser Val Cys Asp Leu Phe Pro Ser Tyr Cys His
305                 310                 315                 320 aac ggc ggc cag tgc tac ctg gtg gac aac ata ggg gcc ttc tgc agg     1008
Asn Gly Gly Gln Cys Tyr Leu Val Asp Asn Ile Gly Ala Phe Cys Arg
                325                 330                 335 tgt aac aca cag gac tac atc tgg cac aag ggg atg cgc tgc gag tcc     1056
Cys Asn Thr Gln Asp Tyr Ile Trp His Lys Gly Met Arg Cys Glu Ser
            340                 345                 350 atc atc acc gac ttc cag gtg atg tgc gtg gcc gtc ggc tca gcc gcc     1104
Ile Ile Thr Asp Phe Gln Val Met Cys Val Ala Val Gly Ser Ala Ala
        355                 360                 365 ctc gtg ctg ctc ctg ctc ttc atg atg aca gtg ttc ttc gcc aag aag     1152
Leu Val Leu Leu Leu Leu Phe Met Met Thr Val Phe Phe Ala Lys Lys
370                 375                 380 ctg tat ctg ctc aag aca gag aat acc aag ctg cgt agg acc aac aaa     1200
Leu Tyr Leu Leu Lys Thr Glu Asn Thr Lys Leu Arg Arg Thr Asn Lys
385                 390                 395                 400 ttc cgg acc ccg tct gag ctc cac aac gat aac ttc tcc ctt tcc acc     1248
Phe Arg Thr Pro Ser Glu Leu His Asn Asp Asn Phe Ser Leu Ser Thr
                405                 410                 415 att gcc gaa ggc tct cac cca aac gac gat ccc agt gct tcc cac aaa     1296
Ile Ala Glu Gly Ser His Pro Asn Asp Asp Pro Ser Ala Ser His Lys
            420                 425                 430 atc cag gag gtt ctc aag tcc tgc ctg aaa gag gag gag tca ttt aac     1344
Ile Gln Glu Val Leu Lys Ser Cys Leu Lys Glu Glu Glu Ser Phe Asn
        435                 440                 445 atc cag aac tcc atg tcc ccc aaa ctg gag ggt ggc aaa ggt gac cag     1392
Ile Gln Asn Ser Met Ser Pro Lys Leu Glu Gly Gly Lys Gly Asp Gln
450                 455                 460 gct gac ttg gag gtg aac tgt ctt cag aac aac ctc acc taa             1434
Ala Asp Leu Glu Val Asn Cys Leu Gln Asn Asn Leu Thr
465                 470                 475 agcagagcaa gaagagaggg aatgggggag ggcgggggt ggcagggaa gaaacatgac    1494 ctcctcttgt acagagtcta tttcttgtaa ccatttgtta aactctcttc ttttctggt    1554 ctcatggcat gccttgatgt attttgtaca ggagggagaa aacacaaaat aagcaaagaa    1614
cctgaacaga atcgcataca ccgggttgtt tcgtctgtgc tgtctgtata ttgcttctgc    1674
```

```
tgctgtgatt tctaaaccta tgctgttatt caactgactt ttttttttgta ctttgaccca    1734 cctttttttg aaataagagt taaaaaacaa agttcttgaa ataaaacttt ttaaaaagcc    1794
attttccatc agtgtgtcca cttcctaccc attcttgtca gcttgagttg aattcttacg    1854
ttccctgaag atgtatattt atatgtgttt gaaatcctgg aagtgctctc tgtattagcc    1914
taggttgccg taactaaaca tcatagactg gatcacttaa gcaatagaaa tttatttttg    1974
aacagtaata gaggctggat ccccaagatc aaggtgccaa cagagttggt ttctggcagg    2034
gcctctctgc ctggcttgca aagagccatc ttcttgctat gtcctcacaa ggccttttgt    2094
ctgtgcacat ctcttcctct tctgataagg acaccagtcc tattggccta ggatccattt    2154
aacctcaatt acctcctcat aggccctact ccagatacag tcacacttag gggttatggc    2214
ttcaacatga cttttggggt gacataattc agtccacaag tctgtagcac ctgatt        2270
```

<210> SEQ ID NO 2
<211> LENGTH: 477
<212> TYPE: PRT
<213> ORGANISM: Canis familiaris

<400> SEQUENCE: 2

```
Gly Glu Glu Glu Thr Ser Cys Thr Ala Pro Gly Gly Leu Pro Ala Val
1               5                   10                  15

Val Gly Pro Gly Val Gly Pro Glu Glu Ala Leu Glu Ala Ser Ala Ala
            20                  25                  30

Val Thr Gly Thr Ala Trp Leu Glu Ala Asp Ser Pro Gly Leu Gly Gly
        35                  40                  45

Ala Thr Val Glu Ala Gly Ser Gly Asp Thr Gln Ala Leu Pro Ala Thr
    50                  55                  60

Leu Pro Thr Pro Glu Glu Ala Leu Arg Arg Ala Ser Val Ala Pro Ala
65                  70                  75                  80

Thr Pro Glu Thr Thr Glu Ala Ser Gly Pro Pro Ser Pro Thr Pro Gly
                85                  90                  95

Asp Gln Leu Arg Pro Gly Pro Glu Leu Pro Lys Glu Ser Pro Leu Glu
            100                 105                 110

Val Trp Leu Asn Leu Gly Gly Ser Thr His Asp Pro His Gly Pro Glu
        115                 120                 125

Pro Thr Phe Pro Phe Gln Gly Thr Leu Glu Pro Arg Pro Ala Ser Asp
    130                 135                 140

Ile Ile Asp Ile Asp Tyr Phe Glu Gly Leu Asp Gly Glu Gly Arg Gly
145                 150                 155                 160

Ala Asp Leu Gly Ser Phe Pro Val Ser Pro Gly Thr Ser Glu His His
                165                 170                 175

Pro Asp Thr Gly Gly Glu Thr Pro Ser Trp Ser Leu Leu Asp Leu Tyr
            180                 185                 190

Asp Asp Phe Thr Pro Phe Asp Glu Ser Asp Phe Tyr Pro Thr Thr Ser
        195                 200                 205

Phe Tyr Asp Asp Leu Glu Glu Glu Glu Glu Asp Asp Asp Lys
    210                 215                 220

Asp Ala Ala Glu Gly Gly Asp Leu Glu Asp Glu Ser Asp Leu Leu Val
225                 230                 235                 240

Pro Thr Glu Lys Pro Gly Leu Arg Pro Gly Pro Gly Gln Pro Thr Ser
                245                 250                 255

Arg Trp His Ala Val Pro Pro Gln His Thr Leu Gly Leu Val Pro Gly
            260                 265                 270
```

```
Ser Ser Ile Ala Leu Arg Pro Arg Pro Gly Glu Pro Gly Arg Asp Leu
        275                 280                 285

Ala Pro Ser Glu Asn Gly Thr Glu Cys Arg Ser Gly Phe Val Arg His
    290                 295                 300

Asn Gly Ser Cys Arg Ser Val Cys Asp Leu Phe Pro Ser Tyr Cys His
305                 310                 315                 320

Asn Gly Gly Gln Cys Tyr Leu Val Asp Asn Ile Gly Ala Phe Cys Arg
                325                 330                 335

Cys Asn Thr Gln Asp Tyr Ile Trp His Lys Gly Met Arg Cys Glu Ser
                340                 345                 350

Ile Ile Thr Asp Phe Gln Val Met Cys Val Ala Val Gly Ser Ala Ala
                355                 360                 365

Leu Val Leu Leu Leu Leu Phe Met Met Thr Val Phe Phe Ala Lys Lys
            370                 375                 380

Leu Tyr Leu Leu Lys Thr Glu Asn Thr Lys Leu Arg Arg Thr Asn Lys
385                 390                 395                 400

Phe Arg Thr Pro Ser Glu Leu His Asn Asp Asn Phe Ser Leu Ser Thr
                405                 410                 415

Ile Ala Glu Gly Ser His Pro Asn Asp Asp Pro Ser Ala Ser His Lys
                420                 425                 430

Ile Gln Glu Val Leu Lys Ser Cys Leu Lys Glu Glu Ser Phe Asn
            435                 440                 445

Ile Gln Asn Ser Met Ser Pro Lys Leu Glu Gly Gly Lys Gly Asp Gln
        450                 455                 460

Ala Asp Leu Glu Val Asn Cys Leu Gln Asn Asn Leu Thr
465                 470                 475

<210> SEQ ID NO 3
<211> LENGTH: 2175
<212> TYPE: DNA
<213> ORGANISM: Homo sapiens
<220> FEATURE:
<221> NAME/KEY: CDS
<222> LOCATION: (177)..(1796)
<223> OTHER INFORMATION:

<400> SEQUENCE: 3
ggggaggcgc ggcgcgccgg ggacagcggc ggacggcggc ggcggcggca tgcggctcct    60
cgcgctgccc atcgtgggct gaggcggccg cagaaccggg gggaggcgcg gcggccgggc   120
gagccgaggg cgcagccagc cgggcggacc gcggacagcg gtcggggcgc cgcgcc atg   179
                                                                Met
                                                                1 ggg cga gcc ggg ggc ggg ggc ccg ggc cgg ggg ccg ccg cca ctg ctg   227
Gly Arg Ala Gly Gly Gly Gly Pro Gly Arg Gly Pro Pro Pro Leu Leu
        5                   10                  15 ctg ttt ctg ggg gcc gcg ctg gtc ctg gcc tct ggg gcc gtg ccg gcg   275
Leu Phe Leu Gly Ala Ala Leu Val Leu Ala Ser Gly Ala Val Pro Ala
            20                  25                  30 cgt gag gcg ggc agc gcg gtt gag gcc gaa gag ctg gtg aag ggc agc   323
Arg Glu Ala Gly Ser Ala Val Glu Ala Glu Glu Leu Val Lys Gly Ser
    35                  40                  45 ccg gcg tgg gag ccg cct gcc aac gac acg cgg gaa gaa gcc ggc cca   371
Pro Ala Trp Glu Pro Pro Ala Asn Asp Thr Arg Glu Glu Ala Gly Pro
50                  55                  60                  65 cca gcg gct ggg gaa gat gag gcg tcg tgg acg gcg ccc ggt ggc gag   419
Pro Ala Ala Gly Glu Asp Glu Ala Ser Trp Thr Ala Pro Gly Gly Glu
                70                  75                  80
```

```
ctg gcc ggg cca gaa gag gtg ctg cag gag tcg gct gcg gtg acc ggc      467
Leu Ala Gly Pro Glu Glu Val Leu Gln Glu Ser Ala Ala Val Thr Gly
            85                  90                  95 acc gcc tgg ctg gaa gct gac agc cca ggc ctg gga gga gtg acc gca      515
Thr Ala Trp Leu Glu Ala Asp Ser Pro Gly Leu Gly Gly Val Thr Ala
        100                 105                 110 gag gcg ggc agc ggc gat gcc cag gcc ctt cca gct acg ctc cag gct      563
Glu Ala Gly Ser Gly Asp Ala Gln Ala Leu Pro Ala Thr Leu Gln Ala
    115                 120                 125 ccc cac gag gtc ctc ggg cag tca atc atg ccc cct gcc att cct gag      611
Pro His Glu Val Leu Gly Gln Ser Ile Met Pro Pro Ala Ile Pro Glu
130                 135                 140                 145 gct aca gag gcc agc ggg cca ccc tcc ccc acc ccc ggc gac aag ctg      659
Ala Thr Glu Ala Ser Gly Pro Pro Ser Pro Thr Pro Gly Asp Lys Leu
                150                 155                 160 agc cca gct tct gaa ctc ccc aag gag agc ccc ttg gag gtt tgg ctg      707
Ser Pro Ala Ser Glu Leu Pro Lys Glu Ser Pro Leu Glu Val Trp Leu
            165                 170                 175 aac ctg ggg ggc agc aca ccc gac cct caa ggg cca gag ctg act tac      755
Asn Leu Gly Gly Ser Thr Pro Asp Pro Gln Gly Pro Glu Leu Thr Tyr
        180                 185                 190 cca ttt cag ggc acc ctg gag ccc caa ccg gca tca gat atc att gac      803
Pro Phe Gln Gly Thr Leu Glu Pro Gln Pro Ala Ser Asp Ile Ile Asp
195                 200                 205 atc gac tac ttc gaa gga ctg gat ggt gag ggt cgt ggc gca gat ctg      851
Ile Asp Tyr Phe Glu Gly Leu Asp Gly Glu Gly Arg Gly Ala Asp Leu
210                 215                 220                 225 ggg agc ttc cca ggg tca cca gga acc tca gag aac cac cct gat act      899
Gly Ser Phe Pro Gly Ser Pro Gly Thr Ser Glu Asn His Pro Asp Thr
                230                 235                 240 gag gga gag acc cct tcc tgg agc ctg ctt gac tta tac gat gat ttc      947
Glu Gly Glu Thr Pro Ser Trp Ser Leu Leu Asp Leu Tyr Asp Asp Phe
            245                 250                 255 acc ccc ttc gat gaa tct gat ttc tac ccc acc aca tcc ttt tat gat      995
Thr Pro Phe Asp Glu Ser Asp Phe Tyr Pro Thr Thr Ser Phe Tyr Asp
        260                 265                 270 gac ttg gat gaa gag gag gag gaa gag gag gat gac aaa gat gca gta     1043
Asp Leu Asp Glu Glu Glu Glu Glu Glu Asp Asp Lys Asp Ala Val
275                 280                 285 gga ggt gga gac cta gaa gat gaa aat gag ctt cta gtg ccc act ggg     1091
Gly Gly Gly Asp Leu Glu Asp Glu Asn Glu Leu Leu Val Pro Thr Gly
290                 295                 300                 305 aag cct ggt ctg ggg ccc ggg aca ggc cag ccc acc agt cgg tgg cat     1139
Lys Pro Gly Leu Gly Pro Gly Thr Gly Gln Pro Thr Ser Arg Trp His
                310                 315                 320 gct gtc cct cca cag cac act ctg ggg tcg gtc ccc ggc agc agc atc     1187
Ala Val Pro Pro Gln His Thr Leu Gly Ser Val Pro Gly Ser Ser Ile
            325                 330                 335 gcc ctc agg ccc cgc cca gga gag cca ggc agg gac ttg gcc tcc agt     1235
Ala Leu Arg Pro Arg Pro Gly Glu Pro Gly Arg Asp Leu Ala Ser Ser
        340                 345                 350 gaa aat ggc act gag tgc cgc agt ggc ttt gtg cgg cat aac ggc tcc     1283
Glu Asn Gly Thr Glu Cys Arg Ser Gly Phe Val Arg His Asn Gly Ser
355                 360                 365 tgc cgg tca gtg tgc gac ctc ttc cca agt tac tgt cac aat ggc ggc     1331
Cys Arg Ser Val Cys Asp Leu Phe Pro Ser Tyr Cys His Asn Gly Gly
370                 375                 380                 385 cag tgc tac ctg gtg gag aac ata ggg gcc ttc tgc agg tgc aac acg     1379
Gln Cys Tyr Leu Val Glu Asn Ile Gly Ala Phe Cys Arg Cys Asn Thr
                390                 395                 400
```

```
cag gac tac atc tgg cac aag ggg atg cgc tgc gag tcc atc atc acc    1427
Gln Asp Tyr Ile Trp His Lys Gly Met Arg Cys Glu Ser Ile Ile Thr
            405                 410                 415 gac ttc cag gtg atg tgc gtg gcc gtg ggc tcg gct gcc ctc gtc ctg    1475
Asp Phe Gln Val Met Cys Val Ala Val Gly Ser Ala Ala Leu Val Leu
        420                 425                 430 ctc ctg ctc ttc atg atg acg gtg ttc ttt gcc aag aag ctc tac ctg    1523
Leu Leu Leu Phe Met Met Thr Val Phe Phe Ala Lys Lys Leu Tyr Leu
435                 440                 445 ctc aag acg gag aat acc aag ctg cgt agg acc aac aaa ttc cgg acc    1571
Leu Lys Thr Glu Asn Thr Lys Leu Arg Arg Thr Asn Lys Phe Arg Thr
450                 455                 460                 465 cca tct gag ctc cac aat gat aac ttc tcc ctc tcc acc att gcc gag    1619
Pro Ser Glu Leu His Asn Asp Asn Phe Ser Leu Ser Thr Ile Ala Glu
                470                 475                 480 ggc tct cac cca aat gat gat cct agt gct ccc cac aaa atc cag gag    1667
Gly Ser His Pro Asn Asp Asp Pro Ser Ala Pro His Lys Ile Gln Glu
            485                 490                 495 gtt ctc aag tcc tgc ctg aaa gag gag gag tca ttt aac atc cag aac    1715
Val Leu Lys Ser Cys Leu Lys Glu Glu Glu Ser Phe Asn Ile Gln Asn
        500                 505                 510 tcc atg tcg ccc aaa ctt gag ggt ggc aaa ggt gac cag gct gac ttg    1763
Ser Met Ser Pro Lys Leu Glu Gly Gly Lys Gly Asp Gln Ala Asp Leu
    515                 520                 525 gat gtg aac tgt ctt cag aat aat tta acc taa agcagagcaa gaagagagga  1816
Asp Val Asn Cys Leu Gln Asn Asn Leu Thr
530                 535 agcgggggta gtgggtgggg ggtaggggaa gaaacattat ctcctcttgt acagagtcta  1876
tttcttgtaa ccatttgtta aactctttc tttttctgat ctcatggcat gcttttatgt   1936
attttgtaca ggaggcaaaa aaatacttaa aataagcaaa gaaactgaac agaattgcat  1996
acattgggtt gttttttctg tgctgtctgt acattgcttc tgctgctgtg atttctaaac  2056
ctgtgctgtt attcaactga cttttttttg tactttgacc cacgtttttt tgaaatacca  2116
gtaaaaaaca aagttcttga aataaaactt tttaaaagt taaaaaaaaa aaaaaaaa     2175

<210> SEQ ID NO 4
<211> LENGTH: 539
<212> TYPE: PRT
<213> ORGANISM: Homo sapiens

<400> SEQUENCE: 4

Met Gly Arg Ala Gly Gly Gly Pro Gly Arg Gly Pro Pro Leu
1               5                   10                  15

Leu Leu Phe Leu Gly Ala Ala Leu Val Leu Ala Ser Gly Ala Val Pro
            20                  25                  30

Ala Arg Glu Ala Gly Ser Ala Val Glu Ala Glu Leu Val Lys Gly
        35                  40                  45

Ser Pro Ala Trp Glu Pro Ala Asn Asp Thr Arg Glu Glu Ala Gly
    50                  55                  60

Pro Pro Ala Ala Gly Glu Asp Glu Ala Ser Trp Thr Ala Pro Gly Gly
65                  70                  75                  80

Glu Leu Ala Gly Pro Glu Val Leu Gln Ser Ala Ala Val Thr
            85                  90                  95

Gly Thr Ala Trp Leu Glu Ala Asp Ser Pro Gly Leu Gly Gly Val Thr
        100                 105                 110

Ala Glu Ala Gly Ser Gly Asp Ala Gln Ala Leu Pro Ala Thr Leu Gln
```

```
              115                 120                 125
Ala Pro His Glu Val Leu Gly Gln Ser Ile Met Pro Pro Ala Ile Pro
130                 135                 140
Glu Ala Thr Glu Ala Ser Gly Pro Pro Ser Pro Thr Pro Gly Asp Lys
145                 150                 155                 160
Leu Ser Pro Ala Ser Glu Leu Pro Lys Glu Ser Pro Leu Glu Val Trp
                165                 170                 175
Leu Asn Leu Gly Gly Ser Thr Pro Asp Pro Gln Gly Pro Glu Leu Thr
            180                 185                 190
Tyr Pro Phe Gln Gly Thr Leu Glu Pro Gln Pro Ala Ser Asp Ile Ile
            195                 200                 205
Asp Ile Asp Tyr Phe Glu Gly Leu Asp Gly Glu Gly Arg Gly Ala Asp
210                 215                 220
Leu Gly Ser Phe Pro Gly Ser Pro Gly Thr Ser Glu Asn His Pro Asp
225                 230                 235                 240
Thr Glu Gly Glu Thr Pro Ser Trp Ser Leu Leu Asp Leu Tyr Asp Asp
                245                 250                 255
Phe Thr Pro Phe Asp Glu Ser Asp Phe Tyr Pro Thr Thr Ser Phe Tyr
                260                 265                 270
Asp Asp Leu Asp Glu Glu Glu Glu Glu Asp Lys Asp Ala
            275                 280                 285
Val Gly Gly Asp Leu Glu Asp Glu Asn Glu Leu Leu Val Pro Thr
290                 295                 300
Gly Lys Pro Gly Leu Gly Pro Gly Thr Gly Gln Pro Thr Ser Arg Trp
305                 310                 315                 320
His Ala Val Pro Pro Gln His Thr Leu Gly Ser Val Pro Gly Ser Ser
                325                 330                 335
Ile Ala Leu Arg Pro Arg Pro Gly Glu Pro Gly Arg Asp Leu Ala Ser
            340                 345                 350
Ser Glu Asn Gly Thr Glu Cys Arg Ser Gly Phe Val Arg His Asn Gly
            355                 360                 365
Ser Cys Arg Ser Val Cys Asp Leu Phe Pro Ser Tyr Cys His Asn Gly
            370                 375                 380
Gly Gln Cys Tyr Leu Val Glu Asn Ile Gly Ala Phe Cys Arg Cys Asn
385                 390                 395                 400
Thr Gln Asp Tyr Ile Trp His Lys Gly Met Arg Cys Glu Ser Ile Ile
                405                 410                 415
Thr Asp Phe Gln Val Met Cys Val Ala Val Gly Ser Ala Ala Leu Val
                420                 425                 430
Leu Leu Leu Leu Phe Met Met Thr Val Phe Phe Ala Lys Lys Leu Tyr
            435                 440                 445
Leu Leu Lys Thr Glu Asn Thr Lys Leu Arg Arg Thr Asn Lys Phe Arg
            450                 455                 460
Thr Pro Ser Glu Leu His Asn Asp Asn Phe Ser Leu Ser Thr Ile Ala
465                 470                 475                 480
Glu Gly Ser His Pro Asn Asp Asp Pro Ser Ala Pro His Lys Ile Gln
                485                 490                 495
Glu Val Leu Lys Ser Cys Leu Lys Glu Glu Ser Phe Asn Ile Gln
            500                 505                 510
Asn Ser Met Ser Pro Lys Leu Glu Gly Gly Lys Gly Asp Gln Ala Asp
            515                 520                 525
Leu Asp Val Asn Cys Leu Gln Asn Asn Leu Thr
            530                 535
```

<210> SEQ ID NO 5
<211> LENGTH: 2253
<212> TYPE: DNA
<213> ORGANISM: Homo sapiens
<220> FEATURE:
<221> NAME/KEY: CDS
<222> LOCATION: (669)..(1874)
<223> OTHER INFORMATION:

<400> SEQUENCE: 5

```
agtccagtga ggaataactg tagataagat gagatgatgg gcattaagtg taactgctga      60
gaagccttca tagagggaaa ggtgataaga actgagtttt tctggcatga ggagtttacc     120
aggcaggaga ggtggagacg ctaggctagg caaataggct gcagccatag ttctgctgag     180
aaacaggttt tgaaccaagg caactccatc tggagatatg tatcagaaag attaggagat     240
agaatctcca tcttggtcac ttatttggtc ttctaagaca gcaatgggac cgtctcttaa     300
atactggagt tgtcctatct ccttgggctg ataccctgaa ctgtcatttg gcgcgtgagg     360
cgggcagcgc ggttgaggcc gaagagctgg tgaagggcag cccggcgtgg gagccgcctg     420
ccaacgacac gcgggaagaa gccggcccac cagcggctgg ggaagatgag gcgtcgtgga     480
cggcgcccgg tggcgagctg gccgggccag aagaggtgct gcaggagtcg gctgcggtga     540
ccggcaccgc ctggctggaa gctgacagcc caggcctggg aggagtgacc gcagaggcgg     600
gcagcggcga tgcccaggcc cttccagcta cgctccaggc tccccacgag gtcctcgggc     660 agtcaatc atg ccc cct gcc att cct gag gct aca gag gcc agc ggg cca      710
         Met Pro Pro Ala Ile Pro Glu Ala Thr Glu Ala Ser Gly Pro
          1               5                  10 ccc tcc ccc acc ccc ggc gac aag ctg agc cca gct tct gaa ctc ccc       758
Pro Ser Pro Thr Pro Gly Asp Lys Leu Ser Pro Ala Ser Glu Leu Pro
 15                  20                  25                  30 aag gag agc ccc ttg gag gtt tgg ctg aac ctg ggg ggc agc aca ccc       806
Lys Glu Ser Pro Leu Glu Val Trp Leu Asn Leu Gly Gly Ser Thr Pro
             35                  40                  45 gac cct caa ggg cca gag ctg act tac cca ttt cag ggc acc ctg gag       854
Asp Pro Gln Gly Pro Glu Leu Thr Tyr Pro Phe Gln Gly Thr Leu Glu
         50                  55                  60 ccc caa ccg gca tca gat atc att gac atc gac tac ttc gaa gga ctg       902
Pro Gln Pro Ala Ser Asp Ile Ile Asp Ile Asp Tyr Phe Glu Gly Leu
 65                  70                  75 gat ggt gag ggt cgt ggc gca gat ctg ggg agc ttc cca ggg tca cca       950
Asp Gly Glu Gly Arg Gly Ala Asp Leu Gly Ser Phe Pro Gly Ser Pro
     80                  85                  90 gga acc tca gag aac cac cct gat act gag gga gag acc cct tcc tgg       998
Gly Thr Ser Glu Asn His Pro Asp Thr Glu Gly Glu Thr Pro Ser Trp
 95                 100                 105                 110 agc ctg ctt gac tta tac gat gat ttc acc ccc ttc gat gaa tct gat      1046
Ser Leu Leu Asp Leu Tyr Asp Asp Phe Thr Pro Phe Asp Glu Ser Asp
            115                 120                 125 ttc tac ccc acc aca tcc ttt tat gat gac ttg gat gaa gag gag gag      1094
Phe Tyr Pro Thr Thr Ser Phe Tyr Asp Asp Leu Asp Glu Glu Glu Glu
        130                 135                 140 gaa gag gag gat gac aaa gat gca gta gga ggt gga gac cta gaa gat      1142
Glu Glu Glu Asp Asp Lys Asp Ala Val Gly Gly Gly Asp Leu Glu Asp
    145                 150                 155 gaa aat gag ctt cta gtg ccc act ggg aag cct ggt ctg ggg ccc ggg      1190
Glu Asn Glu Leu Leu Val Pro Thr Gly Lys Pro Gly Leu Gly Pro Gly
160                 165                 170
```

```
aca ggc cag ccc acc agt cgg tgg cat gct gtc cct cca cag cac act   1238
Thr Gly Gln Pro Thr Ser Arg Trp His Ala Val Pro Pro Gln His Thr
175                 180                 185                 190 ctg ggg tcg gtc ccc ggc agc agc atc gcc ctc agg ccc cgc cca gga   1286
Leu Gly Ser Val Pro Gly Ser Ser Ile Ala Leu Arg Pro Arg Pro Gly
                195                 200                 205 gag cca ggc agg gac ttg gcc tcc agt gaa aat ggc act gag tgc cgc   1334
Glu Pro Gly Arg Asp Leu Ala Ser Ser Glu Asn Gly Thr Glu Cys Arg
            210                 215                 220 agt ggc ttt gtg cgg cat aac ggc tcc tgc cgg tca gtg tgc gac ctc   1382
Ser Gly Phe Val Arg His Asn Gly Ser Cys Arg Ser Val Cys Asp Leu
225                 230                 235 ttc cca agt tac tgt cac aat ggc ggc cag tgc tac ctg gtg gag aac   1430
Phe Pro Ser Tyr Cys His Asn Gly Gly Gln Cys Tyr Leu Val Glu Asn
    240                 245                 250 ata ggg gcc ttc tgc agg tgc aac acg cag gac tac atc tgg cac aag   1478
Ile Gly Ala Phe Cys Arg Cys Asn Thr Gln Asp Tyr Ile Trp His Lys
255                 260                 265                 270 ggg atg cgc tgc gag tcc atc atc acc gac ttc cag gtg atg tgc gtg   1526
Gly Met Arg Cys Glu Ser Ile Ile Thr Asp Phe Gln Val Met Cys Val
                275                 280                 285 gcc gtg ggc tcg gct gcc ctc gtc ctg ctc ctg ttc atg atg acg       1574
Ala Val Gly Ser Ala Ala Leu Val Leu Leu Leu Phe Met Met Thr
            290                 295                 300 gtg ttc ttt gcc aag aag ctc tac ctg ctc aag acg gag aat acc aag   1622
Val Phe Phe Ala Lys Lys Leu Tyr Leu Leu Lys Thr Glu Asn Thr Lys
        305                 310                 315 ctg cgt agg acc aac aaa ttc cgg acc cca tct gag ctc cac aat gat   1670
Leu Arg Arg Thr Asn Lys Phe Arg Thr Pro Ser Glu Leu His Asn Asp
    320                 325                 330 aac ttc tcc ctc tcc acc att gcc gag ggc tct cac cca aat gat gat   1718
Asn Phe Ser Leu Ser Thr Ile Ala Glu Gly Ser His Pro Asn Asp Asp
335                 340                 345                 350 cct agt gct ccc cac aaa atc cag gag gtt ctc aag tcc tgc ctg aaa   1766
Pro Ser Ala Pro His Lys Ile Gln Glu Val Leu Lys Ser Cys Leu Lys
                355                 360                 365 gag gag gag tca ttt aac atc cag aac tcc atg tcg ccc aaa ctt gag   1814
Glu Glu Glu Ser Phe Asn Ile Gln Asn Ser Met Ser Pro Lys Leu Glu
            370                 375                 380 ggt ggc aaa ggt gac cag gct gac ttg gat gtg aac tgt ctt cag aat   1862
Gly Gly Lys Gly Asp Gln Ala Asp Leu Asp Val Asn Cys Leu Gln Asn
        385                 390                 395 aat tta acc taa agcagagcaa gaagagagga agcgggggta gtgggtgggg       1914
Asn Leu Thr
        400 ggtaggggaa gaaacattat ctcctcttgt acagagtcta tttcttgtaa ccatttgtta   1974 aactctttc  ttttctgat  ctcatggcat gcttttatgt attttgtaca ggaggcaaaa   2034 aaatacttaa aataagcaaa gaaactgaac agaattgcat acattgggtt gttttttctg   2094 tgctgtctgt acattgcttc tgctgctgtg atttctaaac ctgtgctgtt attcaactga   2154 cttttttttg tactttgacc cacgtttttt tgaaatacca gtaaaaaaca aagttcttga   2214 aataaaactt tttaaaaagt taaaaaaaaa aaaaaaaa                           2253
```

<210> SEQ ID NO 6
<211> LENGTH: 401
<212> TYPE: PRT
<213> ORGANISM: Homo sapiens

<400> SEQUENCE: 6

```
Met Pro Pro Ala Ile Pro Glu Ala Thr Glu Ala Ser Gly Pro Pro Ser
1               5                   10                  15

Pro Thr Pro Gly Asp Lys Leu Ser Pro Ala Ser Glu Leu Pro Lys Glu
            20                  25                  30

Ser Pro Leu Glu Val Trp Leu Asn Leu Gly Ser Thr Pro Asp Pro
        35                  40                  45

Gln Gly Pro Glu Leu Thr Tyr Pro Phe Gln Gly Thr Leu Glu Pro Gln
50                      55                  60

Pro Ala Ser Asp Ile Ile Asp Ile Asp Tyr Phe Glu Gly Leu Asp Gly
65                  70                  75                  80

Glu Gly Arg Gly Ala Asp Leu Gly Ser Phe Pro Gly Ser Pro Gly Thr
                85                  90                  95

Ser Glu Asn His Pro Asp Thr Glu Gly Glu Thr Pro Ser Trp Ser Leu
                100                 105                 110

Leu Asp Leu Tyr Asp Asp Phe Thr Pro Phe Asp Glu Ser Asp Phe Tyr
        115                 120                 125

Pro Thr Thr Ser Phe Tyr Asp Asp Leu Asp Glu Glu Glu Glu Glu
130                 135                 140

Glu Asp Asp Lys Asp Ala Val Gly Gly Asp Leu Glu Asp Glu Asn
145                 150                 155                 160

Glu Leu Leu Val Pro Thr Gly Lys Pro Gly Leu Gly Pro Gly Thr Gly
                165                 170                 175

Gln Pro Thr Ser Arg Trp His Ala Val Pro Pro Gln His Thr Leu Gly
                180                 185                 190

Ser Val Pro Gly Ser Ser Ile Ala Leu Arg Pro Arg Pro Gly Glu Pro
        195                 200                 205

Gly Arg Asp Leu Ala Ser Ser Glu Asn Gly Thr Glu Cys Arg Ser Gly
210                 215                 220

Phe Val Arg His Asn Gly Ser Cys Arg Ser Val Cys Asp Leu Phe Pro
225                 230                 235                 240

Ser Tyr Cys His Asn Gly Gly Gln Cys Tyr Leu Val Glu Asn Ile Gly
            245                 250                 255

Ala Phe Cys Arg Cys Asn Thr Gln Asp Tyr Ile Trp His Lys Gly Met
        260                 265                 270

Arg Cys Glu Ser Ile Ile Thr Asp Phe Gln Val Met Cys Val Ala Val
        275                 280                 285

Gly Ser Ala Ala Leu Val Leu Leu Leu Phe Met Met Thr Val Phe
    290                 295                 300

Phe Ala Lys Lys Leu Tyr Leu Leu Lys Thr Glu Asn Thr Lys Leu Arg
305                 310                 315                 320

Arg Thr Asn Lys Phe Arg Thr Pro Ser Glu Leu His Asn Asp Asn Phe
            325                 330                 335

Ser Leu Ser Thr Ile Ala Glu Gly Ser His Pro Asn Asp Asp Pro Ser
            340                 345                 350

Ala Pro His Lys Ile Gln Glu Val Leu Lys Ser Cys Leu Lys Glu Glu
        355                 360                 365

Glu Ser Phe Asn Ile Gln Asn Ser Met Ser Pro Lys Leu Glu Gly Gly
        370                 375                 380

Lys Gly Asp Gln Ala Asp Leu Asp Val Asn Cys Leu Gln Asn Asn Leu
385                 390                 395                 400

Thr
```

-continued

```
<210> SEQ ID NO 7
<211> LENGTH: 2256
<212> TYPE: DNA
<213> ORGANISM: Homo sapiens
<220> FEATURE:
<221> NAME/KEY: CDS
<222> LOCATION: (177)..(1877)
<223> OTHER INFORMATION:

<400> SEQUENCE: 7
ggggaggcgc ggcgcgccgg ggacagcggc ggacggcggc ggcggcggca tgcgggctcct        60 cgcgctgccc atcgtgggct gaggcggccg cagaaccggc gggaggcgcg gcggccgggc       120
gagccgaggg cgcagccagc cgggcggacc gcggacagcg gtcggggcgc cgcgcc atg       179
                                                                  Met
                                                                   1 ggg cga gcc ggg ggc ggg ggc ccg ggc cgg ggg ccg ccg cca ctg ctg        227
Gly Arg Ala Gly Gly Gly Gly Pro Gly Arg Gly Pro Pro Pro Leu Leu
            5                   10                  15 ctg ttt ctg ggg gcc gcg ctg gtc ctg gcc tct ggg gcc gtg ccg gcg        275
Leu Phe Leu Gly Ala Ala Leu Val Leu Ala Ser Gly Ala Val Pro Ala
        20                  25                  30 cgt gag gcg ggc agc gcg gtt gag gcc gaa gag ctg gtg aag ggc agc        323
Arg Glu Ala Gly Ser Ala Val Glu Ala Glu Glu Leu Val Lys Gly Ser
    35                  40                  45 ccg gcg tgg gag ccg cct gcc aac gac acg cgg gaa gaa gcc ggc cca        371
Pro Ala Trp Glu Pro Pro Ala Asn Asp Thr Arg Glu Glu Ala Gly Pro
50                  55                  60                  65 cca gcg gct ggg gaa gat gag gcg tcg tgg acg gcg ccc ggt ggc gag        419
Pro Ala Ala Gly Glu Asp Glu Ala Ser Trp Thr Ala Pro Gly Gly Glu
                70                  75                  80 ctg gcc ggg cca gaa gag gtg ctg cag gag tcg gct gcg gtg acc ggc        467
Leu Ala Gly Pro Glu Glu Val Leu Gln Glu Ser Ala Ala Val Thr Gly
            85                  90                  95 acc gcc tgg ctg gaa gct gac agc cca ggc ctg gga gga gtg acc gca        515
Thr Ala Trp Leu Glu Ala Asp Ser Pro Gly Leu Gly Gly Val Thr Ala
        100                 105                 110 gag gcg ggc agc ggc gat gcc cag gcc ctt cca gct acg ctc cag gct        563
Glu Ala Gly Ser Gly Asp Ala Gln Ala Leu Pro Ala Thr Leu Gln Ala
    115                 120                 125 ccc cac gag gtc ctc ggg cag tca atc atg ccc cct gcc att cct gag        611
Pro His Glu Val Leu Gly Gln Ser Ile Met Pro Pro Ala Ile Pro Glu
130                 135                 140                 145 gct aca gag gcc agc ggg cca ccc tcc ccc acc ccc ggc gac aag ctg        659
Ala Thr Glu Ala Ser Gly Pro Pro Ser Pro Thr Pro Gly Asp Lys Leu
                150                 155                 160 agc cca gct tct gaa ctc ccc aag gag agc ccc ttg gag gtt tgg ctg        707
Ser Pro Ala Ser Glu Leu Pro Lys Glu Ser Pro Leu Glu Val Trp Leu
            165                 170                 175 aac ctg ggg ggc agc aca ccc gac cct caa ggg cca gag ctg act tac        755
Asn Leu Gly Gly Ser Thr Pro Asp Pro Gln Gly Pro Glu Leu Thr Tyr
        180                 185                 190 cca ttt cag ggc acc ctg gag ccc caa ccg gca tca gat atc att gac        803
Pro Phe Gln Gly Thr Leu Glu Pro Gln Pro Ala Ser Asp Ile Ile Asp
    195                 200                 205 atc gac tac ttc gaa gga ctg gat ggt gag ggt cgt ggc gca gat ctg        851
Ile Asp Tyr Phe Glu Gly Leu Asp Gly Glu Gly Arg Gly Ala Asp Leu
210                 215                 220                 225 ggg agc ttc cca ggg tca cca gga acc tca gag aac cac cct gat act        899
Gly Ser Phe Pro Gly Ser Pro Gly Thr Ser Glu Asn His Pro Asp Thr
                230                 235                 240
```

-continued

| | | |
|---|---|---|
| gag gga gag acc cct tcc tgg agc ctg ctt gac tta tac gat gat ttc<br>Glu Gly Glu Thr Pro Ser Trp Ser Leu Leu Asp Leu Tyr Asp Asp Phe<br>                245                      250                            255 | 947 |
| acc ccc ttc gat gaa tct gat ttc tac ccc acc aca tcc ttt tat gat<br>Thr Pro Phe Asp Glu Ser Asp Phe Tyr Pro Thr Thr Ser Phe Tyr Asp<br>           260                            265                        270 | 995 |
| gac ttg gat gaa gag gag gaa gag gag gat gac aaa gat gca gta<br>Asp Leu Asp Glu Glu Glu Glu Glu Glu Asp Asp Lys Asp Ala Val<br>      275                      280                      285 | 1043 |
| gga ggt gga gac cta gaa gat gaa aat gag ctt cta gtg ccc act ggg<br>Gly Gly Gly Asp Leu Glu Asp Glu Asn Glu Leu Leu Val Pro Thr Gly<br>290                      295                      300                      305 | 1091 |
| aag cct ggt ctg ggg ccc ggg aca ggc cag ccc acc agt cgg tgg cat<br>Lys Pro Gly Leu Gly Pro Gly Thr Gly Gln Pro Thr Ser Arg Trp His<br>                310                      315                        320 | 1139 |
| gct gtc cct cca cag cac act ctg ggg tcg gtc ccc ggc agc agc atc<br>Ala Val Pro Pro Gln His Thr Leu Gly Ser Val Pro Gly Ser Ser Ile<br>                325                      330                      335 | 1187 |
| gcc ctc agg ccc cgc cca gga gag cca ggc agg gac ttg gcc tcc agt<br>Ala Leu Arg Pro Arg Pro Gly Glu Pro Gly Arg Asp Leu Ala Ser Ser<br>            340                            345                      350 | 1235 |
| gaa aat ggc act gag tgc cgc agt ggc ttt gtg cgg cat aac ggc tcc<br>Glu Asn Gly Thr Glu Cys Arg Ser Gly Phe Val Arg His Asn Gly Ser<br>         355                      360                      365 | 1283 |
| tgc cgg tca gtg tgc gac ctc ttc cca agt tac tgt cac aat ggc ggc<br>Cys Arg Ser Val Cys Asp Leu Phe Pro Ser Tyr Cys His Asn Gly Gly<br>370                      375                      380                      385 | 1331 |
| cag tgc tac ctg gtg gag aac ata ggg gcc ttc tgc agg tgc aac acg<br>Gln Cys Tyr Leu Val Glu Asn Ile Gly Ala Phe Cys Arg Cys Asn Thr<br>                390                      395                        400 | 1379 |
| cag gac tac atc tgg cac aag ggg atg cgc tgc gag tcc atc atc acc<br>Gln Asp Tyr Ile Trp His Lys Gly Met Arg Cys Glu Ser Ile Ile Thr<br>            405                            410                      415 | 1427 |
| gac ttc cag gtg atg tgc gtg gcc gtg ggc tcg gct gcc ctc gtc ctg<br>Asp Phe Gln Val Met Cys Val Ala Val Gly Ser Ala Ala Leu Val Leu<br>            420                            425                      430 | 1475 |
| ctc ctg ctc ttc atg atg acg gtg ttc ttt gcc aag aag ctc tac ctg<br>Leu Leu Leu Phe Met Met Thr Val Phe Phe Ala Lys Lys Leu Tyr Leu<br>435                      440                      445 | 1523 |
| ctc aag acg gag aat acc aag ctg cgt agg acc aac aaa ttc cgg acc<br>Leu Lys Thr Glu Asn Thr Lys Leu Arg Arg Thr Asn Lys Phe Arg Thr<br>450                      455                      460                      465 | 1571 |
| cca tct gag ctc cac aat gat aac ttc tcc ctc tcc acc att gcc gag<br>Pro Ser Glu Leu His Asn Asp Asn Phe Ser Leu Ser Thr Ile Ala Glu<br>                470                      475                      480 | 1619 |
| ggc tct cac cca aat gta agg aaa ctt tgc aac act ccc cgt acc tcc<br>Gly Ser His Pro Asn Val Arg Lys Leu Cys Asn Thr Pro Arg Thr Ser<br>                485                      490                      495 | 1667 |
| tcc ccc cat gcc cgt gcc ttg gct cac tat gat aac gtt atc tgt cag<br>Ser Pro His Ala Arg Ala Leu Ala His Tyr Asp Asn Val Ile Cys Gln<br>            500                            505                      510 | 1715 |
| gat gat cct agt gct ccc cac aaa atc cag gag gtt ctc aag tcc tgc<br>Asp Asp Pro Ser Ala Pro His Lys Ile Gln Glu Val Leu Lys Ser Cys<br>515                      520                      525 | 1763 |
| ctg aaa gag gag gag tca ttt aac atc cag aac tcc atg tcg ccc aaa<br>Leu Lys Glu Glu Glu Ser Phe Asn Ile Gln Asn Ser Met Ser Pro Lys<br>530                      535                      540                      545 | 1811 |
| ctt gag ggt ggc aaa ggt gac cag gct gac ttg gat gtg aac tgt ctt<br>Leu Glu Gly Gly Lys Gly Asp Gln Ala Asp Leu Asp Val Asn Cys Leu<br>                550                      555                      560 | 1859 |

-continued

```
cag aat aat tta acc taa agcagagcaa gaagagagga agcgggggta          1907
Gln Asn Asn Leu Thr
            565 gtgggtgggg ggtaggggaa gaaacattat ctcctcttgt acagagtcta tttcttgtaa  1967 ccatttgtta aactcttttc ttttctgat ctcatggcat gcttttatgt attttgtaca   2027 ggagcaaaa aaatacttaa aataagcaaa gaaactgaac agaattgcat acattgggtt   2087 gttttttctg tgctgtctgt acattgcttc tgctgctgtg atttctaaac ctgtgctgtt  2147 attcaactga cttttttttg tactttgacc cacgttttttt tgaaatacca gtaaaaaaca  2207 aagttcttga aataaaactt tttaaaaagt taaaaaaaaa aaaaaaaaa              2256
```

<210> SEQ ID NO 8
<211> LENGTH: 566
<212> TYPE: PRT
<213> ORGANISM: Homo sapiens

<400> SEQUENCE: 8

```
Met Gly Arg Ala Gly Gly Gly Pro Gly Arg Pro Pro Leu
1               5                   10              15

Leu Leu Phe Leu Gly Ala Ala Leu Val Leu Ala Ser Gly Ala Val Pro
            20                  25                  30

Ala Arg Glu Ala Gly Ser Ala Val Glu Ala Glu Leu Val Lys Gly
        35                  40                  45

Ser Pro Ala Trp Glu Pro Pro Ala Asn Asp Thr Arg Glu Glu Ala Gly
    50                  55                  60

Pro Pro Ala Ala Gly Glu Asp Glu Ala Ser Trp Thr Ala Pro Gly Gly
65                  70                  75                  80

Glu Leu Ala Gly Pro Glu Glu Val Leu Gln Glu Ser Ala Ala Val Thr
                85                  90                  95

Gly Thr Ala Trp Leu Glu Ala Asp Ser Pro Gly Leu Gly Val Thr
            100                 105                 110

Ala Glu Ala Gly Ser Gly Asp Ala Gln Ala Leu Pro Ala Thr Leu Gln
        115                 120                 125

Ala Pro His Glu Val Leu Gly Gln Ser Ile Met Pro Ala Ile Pro
    130                 135                 140

Glu Ala Thr Glu Ala Ser Gly Pro Ser Pro Thr Pro Gly Asp Lys
145                 150                 155                 160

Leu Ser Pro Ala Ser Glu Leu Pro Lys Glu Ser Pro Leu Glu Val Trp
                165                 170                 175

Leu Asn Leu Gly Gly Ser Thr Pro Asp Pro Gln Gly Pro Glu Leu Thr
            180                 185                 190

Tyr Pro Phe Gln Gly Thr Leu Glu Pro Gln Pro Ala Ser Asp Ile Ile
        195                 200                 205

Asp Ile Asp Tyr Phe Glu Gly Leu Asp Gly Glu Gly Arg Gly Ala Asp
    210                 215                 220

Leu Gly Ser Phe Pro Gly Ser Pro Gly Thr Ser Glu Asn His Pro Asp
225                 230                 235                 240

Thr Glu Gly Glu Thr Pro Ser Trp Ser Leu Leu Asp Leu Tyr Asp Asp
                245                 250                 255

Phe Thr Pro Phe Asp Glu Ser Asp Phe Tyr Pro Thr Thr Ser Phe Tyr
            260                 265                 270

Asp Asp Leu Asp Glu Glu Glu Glu Glu Glu Asp Asp Lys Asp Ala
        275                 280                 285
```

```
Val Gly Gly Gly Asp Leu Glu Asp Glu Asn Glu Leu Leu Val Pro Thr
290                 295                 300

Gly Lys Pro Gly Leu Gly Pro Gly Thr Gly Gln Pro Thr Ser Arg Trp
305                 310                 315                 320

His Ala Val Pro Pro Gln His Thr Leu Gly Ser Val Pro Gly Ser Ser
                325                 330                 335

Ile Ala Leu Arg Pro Arg Pro Gly Glu Pro Gly Arg Asp Leu Ala Ser
                340                 345                 350

Ser Glu Asn Gly Thr Glu Cys Arg Ser Gly Phe Val Arg His Asn Gly
            355                 360                 365

Ser Cys Arg Ser Val Cys Asp Leu Phe Pro Ser Tyr Cys His Asn Gly
370                 375                 380

Gly Gln Cys Tyr Leu Val Glu Asn Ile Gly Ala Phe Cys Arg Cys Asn
385                 390                 395                 400

Thr Gln Asp Tyr Ile Trp His Lys Gly Met Arg Cys Glu Ser Ile Ile
                405                 410                 415

Thr Asp Phe Gln Val Met Cys Val Ala Val Gly Ser Ala Ala Leu Val
                420                 425                 430

Leu Leu Leu Leu Phe Met Met Thr Val Phe Phe Ala Lys Lys Leu Tyr
            435                 440                 445

Leu Leu Lys Thr Glu Asn Thr Lys Leu Arg Arg Thr Asn Lys Phe Arg
450                 455                 460

Thr Pro Ser Glu Leu His Asn Asp Asn Phe Ser Leu Ser Thr Ile Ala
465                 470                 475                 480

Glu Gly Ser His Pro Asn Val Arg Lys Leu Cys Asn Thr Pro Arg Thr
                485                 490                 495

Ser Ser Pro His Ala Arg Ala Leu Ala His Tyr Asp Asn Val Ile Cys
                500                 505                 510

Gln Asp Asp Pro Ser Ala Pro His Lys Ile Gln Glu Val Leu Lys Ser
            515                 520                 525

Cys Leu Lys Glu Glu Glu Ser Phe Asn Ile Gln Asn Ser Met Ser Pro
530                 535                 540

Lys Leu Glu Gly Gly Lys Gly Asp Gln Ala Asp Leu Asp Val Asn Cys
545                 550                 555                 560

Leu Gln Asn Asn Leu Thr
                565

<210> SEQ ID NO 9
<211> LENGTH: 2099
<212> TYPE: DNA
<213> ORGANISM: Homo sapiens
<220> FEATURE:
<221> NAME/KEY: CDS
<222> LOCATION: (177)..(1610)
<223> OTHER INFORMATION:

<400> SEQUENCE: 9
ggggaggcgc ggcgcgccgg ggacagcggc ggacggcggc ggcggcggca tgcggctcct      60
cgcgctgccc atcgtgggct gaggcggccg cagaaccggc gggaggcgcg gcggccgggc     120
gagccgaggg cgcagccagc cggcggacc gcggacagcg gtcggggcgc cgcgcc atg     179
                                                              Met
                                                                1 ggg cga gcc ggg ggc ggg ggc ccg ggc cgg ggg ccg ccg cca ctg ctg      227
Gly Arg Ala Gly Gly Gly Gly Pro Gly Arg Gly Pro Pro Pro Leu Leu
            5                   10                  15 ctg ttt ctg ggg gcc gcg ctg gtc ctg gcc tct ggg gcc gtg ccg gcg      275
```

```
                Leu Phe Leu Gly Ala Ala Leu Val Leu Ala Ser Gly Ala Val Pro Ala
                        20                  25                  30 cgt gag gcg ggc agc gcg gtt gag gcc gaa gag ctg gtg aag ggc agc              323
Arg Glu Ala Gly Ser Ala Val Glu Ala Glu Glu Leu Val Lys Gly Ser
    35                  40                  45 ccg gcg tgg gag ccg cct gcc aac gac acg cgg gaa gaa gcc ggc cca              371
Pro Ala Trp Glu Pro Pro Ala Asn Asp Thr Arg Glu Glu Ala Gly Pro
50                  55                  60                  65 cca gcg gct ggg gaa gat gag gcg tcg tgg acg gcg ccc ggt ggc gag              419
Pro Ala Ala Gly Glu Asp Glu Ala Ser Trp Thr Ala Pro Gly Gly Glu
                70                  75                  80 ctg gcc ggg cca gaa gag gtg ctg cag gag tcg gct gcg gtg acc ggc              467
Leu Ala Gly Pro Glu Glu Val Leu Gln Glu Ser Ala Ala Val Thr Gly
        85                  90                  95 acc gcc tgg ctg gaa gct gac agc cca ggc ctg gga gga gtg acc gca              515
Thr Ala Trp Leu Glu Ala Asp Ser Pro Gly Leu Gly Gly Val Thr Ala
    100                 105                 110 gag gcg ggc agc ggc gat gcc cag gcc ctt cca gct acg ctc cag gct              563
Glu Ala Gly Ser Gly Asp Ala Gln Ala Leu Pro Ala Thr Leu Gln Ala
115                 120                 125 ccc cac gag gtc ctc ggg cag tca atc atg ccc cct gcc att cct gag              611
Pro His Glu Val Leu Gly Gln Ser Ile Met Pro Pro Ala Ile Pro Glu
130                 135                 140                 145 gct aca gag gcc agc ggg cca ccc tcc ccc acc ccc ggc gac aag ctg              659
Ala Thr Glu Ala Ser Gly Pro Pro Ser Pro Thr Pro Gly Asp Lys Leu
                150                 155                 160 agc cca gct tct gaa ctc ccc aag gag agc ccc ttg gag gtt tgg ctg              707
Ser Pro Ala Ser Glu Leu Pro Lys Glu Ser Pro Leu Glu Val Trp Leu
        165                 170                 175 aac ctg ggg ggc agc aca ccc gac cct caa ggg cca gag ctg act tac              755
Asn Leu Gly Gly Ser Thr Pro Asp Pro Gln Gly Pro Glu Leu Thr Tyr
    180                 185                 190 cca ttt cag ggc acc ctg gag ccc caa ccg gca tca gat atc att gac              803
Pro Phe Gln Gly Thr Leu Glu Pro Gln Pro Ala Ser Asp Ile Ile Asp
195                 200                 205 atc gac tac ttc gaa gga ctg gat ggt gag ggt cgt ggc gca gat ctg              851
Ile Asp Tyr Phe Glu Gly Leu Asp Gly Glu Gly Arg Gly Ala Asp Leu
210                 215                 220                 225 ggg agc ttc cca ggg tca cca gga acc tca gag aac cac cct gat act              899
Gly Ser Phe Pro Gly Ser Pro Gly Thr Ser Glu Asn His Pro Asp Thr
                230                 235                 240 gag gga gag acc cct tcc tgg agc ctg ctt gac tta tac gat gat ttc              947
Glu Gly Glu Thr Pro Ser Trp Ser Leu Leu Asp Leu Tyr Asp Asp Phe
        245                 250                 255 acc ccc ttc gat gaa tct gat ttc tac ccc acc aca tcc ttt tat gat              995
Thr Pro Phe Asp Glu Ser Asp Phe Tyr Pro Thr Thr Ser Phe Tyr Asp
    260                 265                 270 gac ttg gat gaa gag gag gag gaa gag gag gat gac aaa gat gca gta              1043
Asp Leu Asp Glu Glu Glu Glu Glu Glu Asp Asp Lys Asp Ala Val
275                 280                 285 gga ggt gga gac cta gaa gat gaa aat gag ctt cta gtg ccc act ggg              1091
Gly Gly Gly Asp Leu Glu Asp Glu Asn Glu Leu Leu Val Pro Thr Gly
290                 295                 300                 305 aag cct ggt ctg ggg ccc ggg aca ggc cag ccc acc agt cgg tgg cat              1139
Lys Pro Gly Leu Gly Pro Gly Thr Gly Gln Pro Thr Ser Arg Trp His
                310                 315                 320 gct gtc cct cca cag cac act ctg ggg tcg gtc ccc ggc agc agc atc              1187
Ala Val Pro Pro Gln His Thr Leu Gly Ser Val Pro Gly Ser Ser Ile
        325                 330                 335
```

-continued

```
gcc ctc agg ccc cgc cca gga gag cca ggc agg gac ttg gcc tcc agt    1235
Ala Leu Arg Pro Arg Pro Gly Glu Pro Gly Arg Asp Leu Ala Ser Ser
        340                 345                 350 gaa aat ggc act gag tgc cgc agt ggc ttt gtg cgg cat aac ggc tcc    1283
Glu Asn Gly Thr Glu Cys Arg Ser Gly Phe Val Arg His Asn Gly Ser
355                 360                 365 tgc cgg tca gtg tgc gac ctc ttc cca agt tac tgt cac aat ggc ggc    1331
Cys Arg Ser Val Cys Asp Leu Phe Pro Ser Tyr Cys His Asn Gly Gly
370                 375                 380                 385 cag tgc tac ctg gtg gag aac ata ggg gcc ttc tgc agg tgc aac acg    1379
Gln Cys Tyr Leu Val Glu Asn Ile Gly Ala Phe Cys Arg Cys Asn Thr
            390                 395                 400 cag gac tac atc tgg cac aag ggg atg cgc tgc gag tcc atc atc acc    1427
Gln Asp Tyr Ile Trp His Lys Gly Met Arg Cys Glu Ser Ile Ile Thr
        405                 410                 415 gac ttc cag gtg atg tgc gtg gcc gtg ggc tcg gct gcc ctc gtc ctg    1475
Asp Phe Gln Val Met Cys Val Ala Val Gly Ser Ala Ala Leu Val Leu
    420                 425                 430 ctc ctg ctc ttc atg atg acg gtg ttc ttt gcc aag aag ctc tac ctg    1523
Leu Leu Leu Phe Met Met Thr Val Phe Phe Ala Lys Lys Leu Tyr Leu
435                 440                 445 ctc aag acg gag aat acc aag ctg cgt agg acc aag atg atc cta gtg    1571
Leu Lys Thr Glu Asn Thr Lys Leu Arg Arg Thr Lys Met Ile Leu Val
450                 455                 460                 465 ctc ccc aca aaa tcc agg agg ttc tca agt cct gcc tga aagaggagga    1620
Leu Pro Thr Lys Ser Arg Arg Phe Ser Ser Pro Ala
            470                 475 gtcatttaac atccagaact ccatgtcgcc caaacttgag ggtggcaaag gtgaccaggc    1680
tgacttggat gtgaactgtc ttcagaataa tttaacctaa agcagagcaa gaagagagga    1740
agcgggggta gtgggtgggg ggtaggggaa gaaacattat ctcctcttgt acagagtcta    1800
tttcttgtaa ccatttgtta aactctttc tttttctgat ctcatggcat gcttttatgt    1860
attttgtaca ggaggcaaaa aaatacttaa aataagcaaa gaaactgaac agaattgcat    1920
acattgggtt gttttttctg tgctgtctgt acattgcttc tgctgctgtg atttctaaac    1980
ctgtgctgtt attcaactga cttttttttg tactttgacc cacgtttttt tgaaatacca    2040
gtaaaaaaca aagttcttga aataaaactt tttaaaaagt taaaaaaaaa aaaaaaaa     2099
```

<210> SEQ ID NO 10
<211> LENGTH: 477
<212> TYPE: PRT
<213> ORGANISM: Homo sapiens

<400> SEQUENCE: 10

```
Met Gly Arg Ala Gly Gly Gly Pro Gly Arg Gly Pro Pro Leu
1               5                   10                  15

Leu Leu Phe Leu Gly Ala Ala Leu Val Leu Ala Ser Gly Ala Val Pro
            20                  25                  30

Ala Arg Glu Ala Gly Ser Ala Val Glu Ala Glu Leu Val Lys Gly
        35                  40                  45

Ser Pro Ala Trp Glu Pro Pro Ala Asn Asp Thr Arg Glu Glu Ala Gly
50                  55                  60

Pro Pro Ala Ala Gly Glu Asp Glu Ala Ser Trp Thr Ala Pro Gly Gly
65                  70                  75                  80

Glu Leu Ala Gly Pro Glu Glu Val Leu Gln Glu Ser Ala Ala Val Thr
                85                  90                  95

Gly Thr Ala Trp Leu Glu Ala Asp Ser Pro Gly Leu Gly Gly Val Thr
```

```
                    100                 105                 110
Ala Glu Ala Gly Ser Gly Asp Ala Gln Ala Leu Pro Ala Thr Leu Gln
                115                 120                 125

Ala Pro His Glu Val Leu Gly Gln Ser Ile Met Pro Pro Ala Ile Pro
            130                 135                 140

Glu Ala Thr Glu Ala Ser Gly Pro Pro Ser Pro Thr Pro Gly Asp Lys
145                 150                 155                 160

Leu Ser Pro Ala Ser Glu Leu Pro Lys Glu Ser Pro Leu Glu Val Trp
                165                 170                 175

Leu Asn Leu Gly Gly Ser Thr Pro Asp Pro Gln Gly Pro Glu Leu Thr
            180                 185                 190

Tyr Pro Phe Gln Gly Thr Leu Glu Pro Gln Pro Ala Ser Asp Ile Ile
        195                 200                 205

Asp Ile Asp Tyr Phe Glu Gly Leu Asp Gly Glu Gly Arg Gly Ala Asp
    210                 215                 220

Leu Gly Ser Phe Pro Gly Ser Pro Gly Thr Ser Glu Asn His Pro Asp
225                 230                 235                 240

Thr Glu Gly Glu Thr Pro Ser Trp Ser Leu Leu Asp Leu Tyr Asp Asp
                245                 250                 255

Phe Thr Pro Phe Asp Glu Ser Asp Phe Tyr Pro Thr Thr Ser Phe Tyr
            260                 265                 270

Asp Asp Leu Asp Glu Glu Glu Glu Glu Asp Asp Lys Asp Ala
        275                 280                 285

Val Gly Gly Gly Asp Leu Glu Asp Glu Asn Glu Leu Leu Val Pro Thr
    290                 295                 300

Gly Lys Pro Gly Leu Gly Pro Gly Thr Gly Gln Pro Thr Ser Arg Trp
305                 310                 315                 320

His Ala Val Pro Pro Gln His Thr Leu Gly Ser Val Pro Gly Ser Ser
                325                 330                 335

Ile Ala Leu Arg Pro Arg Pro Gly Glu Pro Gly Arg Asp Leu Ala Ser
            340                 345                 350

Ser Glu Asn Gly Thr Glu Cys Arg Ser Gly Phe Val Arg His Asn Gly
        355                 360                 365

Ser Cys Arg Ser Val Cys Asp Leu Phe Pro Ser Tyr Cys His Asn Gly
    370                 375                 380

Gly Gln Cys Tyr Leu Val Glu Asn Ile Gly Ala Phe Cys Arg Cys Asn
385                 390                 395                 400

Thr Gln Asp Tyr Ile Trp His Lys Gly Met Arg Cys Glu Ser Ile Ile
                405                 410                 415

Thr Asp Phe Gln Val Met Cys Val Ala Val Gly Ser Ala Ala Leu Val
            420                 425                 430

Leu Leu Leu Leu Phe Met Met Thr Val Phe Phe Ala Lys Lys Leu Tyr
        435                 440                 445

Leu Leu Lys Thr Glu Asn Thr Lys Leu Arg Arg Thr Lys Met Ile Leu
    450                 455                 460

Val Leu Pro Thr Lys Ser Arg Arg Phe Ser Ser Pro Ala
465                 470                 475

<210> SEQ ID NO 11
<211> LENGTH: 2334
<212> TYPE: DNA
<213> ORGANISM: Homo sapiens
<220> FEATURE:
<221> NAME/KEY: CDS
<222> LOCATION: (669)..(1955)
```

-continued

<223> OTHER INFORMATION:

<400> SEQUENCE: 11

```
agtccagtga ggaataactg tagataagat gagatgatgg gcattaagtg taactgctga    60
gaagccttca tagagggaaa ggtgataaga actgagtttt tctggcatga ggagtttacc   120
aggcaggaga ggtggagacg ctaggctagg caaataggct gcagccatag ttctgctgag   180
aaacaggttt tgaaccaagg caactccatc tggagatatg tatcagaaag attaggagat   240
agaatctcca tcttggtcac ttatttggtc ttctaagaca gcaatgggac cgtctcttaa   300
atactggagt tgtcctatct ccttgggctg ataccctgaa ctgtcatttg gcgcgtgagg   360
cgggcagcgc ggttgaggcc gaagagctgg tgaagggcag cccggcgtgg gagccgcctg   420
ccaacgacac gcgggaagaa gccggcccac cagcggctgg ggaagatgag gcgtcgtgga   480
cggcgcccgg tggcgagctg gccgggccag aagaggtgct gcaggagtcg gctgcggtga   540
ccggcaccgc ctggctggaa gctgacagcc caggcctggg aggagtgacc gcagaggcgg   600
gcagcggcga tgcccaggcc cttccagcta cgctccaggc tccccacgag gtcctcgggc   660
```

```
agtcaatc atg ccc cct gcc att cct gag gct aca gag gcc agc ggg cca    710
         Met Pro Pro Ala Ile Pro Glu Ala Thr Glu Ala Ser Gly Pro
         1               5                  10 ccc tcc ccc acc ccc ggc gac aag ctg agc cca gct tct gaa ctc ccc    758
Pro Ser Pro Thr Pro Gly Asp Lys Leu Ser Pro Ala Ser Glu Leu Pro
15                  20                  25                  30 aag gag agc ccc ttg gag gtt tgg ctg aac ctg ggg gc agc aca ccc    806
Lys Glu Ser Pro Leu Glu Val Trp Leu Asn Leu Gly Gly Ser Thr Pro
                35                  40                  45 gac cct caa ggg cca gag ctg act tac cca ttt cag ggc acc ctg gag    854
Asp Pro Gln Gly Pro Glu Leu Thr Tyr Pro Phe Gln Gly Thr Leu Glu
            50                  55                  60 ccc caa ccg gca tca gat atc att gac atc gac tac ttc gaa gga ctg    902
Pro Gln Pro Ala Ser Asp Ile Ile Asp Ile Asp Tyr Phe Glu Gly Leu
65                  70                  75 gat ggt gag ggt cgt ggc gca gat ctg ggg agc ttc cca ggg tca cca    950
Asp Gly Glu Gly Arg Gly Ala Asp Leu Gly Ser Phe Pro Gly Ser Pro
80                  85                  90 gga acc tca gag aac cac cct gat act gag gga gag acc cct tcc tgg    998
Gly Thr Ser Glu Asn His Pro Asp Thr Glu Gly Glu Thr Pro Ser Trp
95                  100                 105                 110 agc ctg ctt gac tta tac gat gat ttc acc ccc ttc gat gaa tct gat   1046
Ser Leu Leu Asp Leu Tyr Asp Asp Phe Thr Pro Phe Asp Glu Ser Asp
                115                 120                 125 ttc tac ccc acc aca tcc ttt tat gat gac ttg gat gaa gag gag gag   1094
Phe Tyr Pro Thr Thr Ser Phe Tyr Asp Asp Leu Asp Glu Glu Glu Glu
            130                 135                 140 gaa gag gag gat gac aaa gat gca gta gga ggt gga gac cta gaa gat   1142
Glu Glu Glu Asp Asp Lys Asp Ala Val Gly Gly Gly Asp Leu Glu Asp
145                 150                 155 gaa aat gag ctt cta gtg ccc act ggg aag cct ggt ctg ggg ccc ggg   1190
Glu Asn Glu Leu Leu Val Pro Thr Gly Lys Pro Gly Leu Gly Pro Gly
160                 165                 170 aca ggc cag ccc acc agt cgg tgg cat gct gtc cct cca cag cac act   1238
Thr Gly Gln Pro Thr Ser Arg Trp His Ala Val Pro Pro Gln His Thr
175                 180                 185                 190 ctg ggg tcg gtc ccc ggc agc agc atc gcc ctc agg ccc cgc cca gga   1286
Leu Gly Ser Val Pro Gly Ser Ser Ile Ala Leu Arg Pro Arg Pro Gly
                195                 200                 205 gag cca ggc agg gac ttg gcc tcc agt gaa aat ggc act gag tgc cgc   1334
Glu Pro Gly Arg Asp Leu Ala Ser Ser Glu Asn Gly Thr Glu Cys Arg
```

```
                Glu Pro Gly Arg Asp Leu Ala Ser Ser Glu Asn Gly Thr Glu Cys Arg
                                210                 215                 220 agt ggc ttt gtg cgg cat aac ggc tcc tgc cgg tca gtg tgc gac ctc            1382
Ser Gly Phe Val Arg His Asn Gly Ser Cys Arg Ser Val Cys Asp Leu
            225                 230                 235 ttc cca agt tac tgt cac aat ggc ggc cag tgc tac ctg gtg gag aac            1430
Phe Pro Ser Tyr Cys His Asn Gly Gly Gln Cys Tyr Leu Val Glu Asn
240                 245                 250 ata ggg gcc ttc tgc agg tgc aac acg cag gac tac atc tgg cac aag            1478
Ile Gly Ala Phe Cys Arg Cys Asn Thr Gln Asp Tyr Ile Trp His Lys
255                 260                 265                 270 ggg atg cgc tgc gag tcc atc atc acc gac ttc cag gtg atg tgc gtg            1526
Gly Met Arg Cys Glu Ser Ile Ile Thr Asp Phe Gln Val Met Cys Val
                275                 280                 285 gcc gtg ggc tcg gct gcc ctc gtc ctg ctg ctc ttc atg atg acg            1574
Ala Val Gly Ser Ala Ala Leu Val Leu Leu Leu Phe Met Met Thr
            290                 295                 300 gtg ttc ttt gcc aag aag ctc tac ctg ctc aag acg gag aat acc aag            1622
Val Phe Phe Ala Lys Lys Leu Tyr Leu Leu Lys Thr Glu Asn Thr Lys
                305                 310                 315 ctg cgt agg acc aac aaa ttc cgg acc cca tct gag ctc cac aat gat            1670
Leu Arg Arg Thr Asn Lys Phe Arg Thr Pro Ser Glu Leu His Asn Asp
        320                 325                 330 aac ttc tcc ctc tcc acc att gcc gag ggc tct cac cca aat gta agg            1718
Asn Phe Ser Leu Ser Thr Ile Ala Glu Gly Ser His Pro Asn Val Arg
335                 340                 345                 350 aaa ctt tgc aac act ccc cgt acc tcc tcc ccc cat gcc cgt gcc ttg            1766
Lys Leu Cys Asn Thr Pro Arg Thr Ser Ser Pro His Ala Arg Ala Leu
                355                 360                 365 gct cac tat gat aac gtt atc tgt cag gat gat cct agt gct ccc cac            1814
Ala His Tyr Asp Asn Val Ile Cys Gln Asp Asp Pro Ser Ala Pro His
            370                 375                 380 aaa atc cag gag gtt ctc aag tcc tgc ctg aaa gag gag gag tca ttt            1862
Lys Ile Gln Glu Val Leu Lys Ser Cys Leu Lys Glu Glu Glu Ser Phe
        385                 390                 395 aac atc cag aac tcc atg tcg ccc aaa ctt gag ggt ggc aaa ggt gac            1910
Asn Ile Gln Asn Ser Met Ser Pro Lys Leu Glu Gly Gly Lys Gly Asp
400                 405                 410 cag gct gac ttg gat gtg aac tgt ctt cag aat aat tta acc taa            1955
Gln Ala Asp Leu Asp Val Asn Cys Leu Gln Asn Asn Leu Thr
415                 420                 425 agcagagcaa gaagagagga agcggggta gtgggtgggg ggtaggggaa gaaacattat            2015
ctcctcttgt acagagtcta tttcttgtaa ccatttgtta aactcttttc tttttctgat            2075
ctcatggcat gctttatgt attttgtaca ggaggcaaaa aaatacttaa aataagcaaa            2135
gaaactgaac agaattgcat acattgggtt gttttttctg tgctgtctgt acattgcttc            2195
tgctgctgtg atttctaaac ctgtgctgtt attcaactga cttttttttg tactttgacc            2255 cacgttttt tgaaatacca gtaaaaaaca aagttcttga aataaaactt tttaaaaagt            2315
taaaaaaaaa aaaaaaaa            2334

<210> SEQ ID NO 12
<211> LENGTH: 428
<212> TYPE: PRT
<213> ORGANISM: Homo sapiens

<400> SEQUENCE: 12

Met Pro Pro Ala Ile Pro Glu Ala Thr Glu Ala Ser Gly Pro Pro Ser
1               5                   10                  15
```

```
Pro Thr Pro Gly Asp Lys Leu Ser Pro Ala Ser Glu Leu Pro Lys Glu
            20                  25                  30

Ser Pro Leu Glu Val Trp Leu Asn Leu Gly Gly Ser Thr Pro Asp Pro
        35                  40                  45

Gln Gly Pro Glu Leu Thr Tyr Pro Phe Gln Gly Thr Leu Glu Pro Gln
50                  55                  60

Pro Ala Ser Asp Ile Ile Asp Ile Asp Tyr Phe Glu Gly Leu Asp Gly
65                  70                  75                  80

Glu Gly Arg Gly Ala Asp Leu Gly Ser Phe Pro Gly Ser Pro Gly Thr
                85                  90                  95

Ser Glu Asn His Pro Asp Thr Glu Gly Glu Thr Pro Ser Trp Ser Leu
            100                 105                 110

Leu Asp Leu Tyr Asp Asp Phe Thr Pro Phe Asp Glu Ser Asp Phe Tyr
        115                 120                 125

Pro Thr Thr Ser Phe Tyr Asp Asp Leu Asp Glu Glu Glu Glu Glu Glu
130                 135                 140

Glu Asp Asp Lys Asp Ala Val Gly Gly Gly Asp Leu Glu Asp Glu Asn
145                 150                 155                 160

Glu Leu Leu Val Pro Thr Gly Lys Pro Gly Leu Gly Pro Gly Thr Gly
                165                 170                 175

Gln Pro Thr Ser Arg Trp His Ala Val Pro Pro Gln His Thr Leu Gly
            180                 185                 190

Ser Val Pro Gly Ser Ser Ile Ala Leu Arg Pro Arg Pro Gly Glu Pro
        195                 200                 205

Gly Arg Asp Leu Ala Ser Ser Glu Asn Gly Thr Glu Cys Arg Ser Gly
210                 215                 220

Phe Val Arg His Asn Gly Ser Cys Arg Ser Val Cys Asp Leu Phe Pro
225                 230                 235                 240

Ser Tyr Cys His Asn Gly Gly Gln Cys Tyr Leu Val Glu Asn Ile Gly
                245                 250                 255

Ala Phe Cys Arg Cys Asn Thr Gln Asp Tyr Ile Trp His Lys Gly Met
            260                 265                 270

Arg Cys Glu Ser Ile Ile Thr Asp Phe Gln Val Met Cys Val Ala Val
        275                 280                 285

Gly Ser Ala Ala Leu Val Leu Leu Leu Leu Phe Met Met Thr Val Phe
290                 295                 300

Phe Ala Lys Lys Leu Tyr Leu Leu Lys Thr Glu Asn Thr Lys Leu Arg
305                 310                 315                 320

Arg Thr Asn Lys Phe Arg Thr Pro Ser Glu Leu His Asn Asp Asn Phe
                325                 330                 335

Ser Leu Ser Thr Ile Ala Glu Gly Ser His Pro Asn Val Arg Lys Leu
            340                 345                 350

Cys Asn Thr Pro Arg Thr Ser Ser Pro His Ala Arg Ala Leu Ala His
        355                 360                 365

Tyr Asp Asn Val Ile Cys Gln Asp Pro Ser Ala Pro His Lys Ile
370                 375                 380

Gln Glu Val Leu Lys Ser Cys Leu Lys Glu Glu Ser Phe Asn Ile
385                 390                 395                 400

Gln Asn Ser Met Ser Pro Lys Leu Glu Gly Gly Lys Gly Asp Gln Ala
                405                 410                 415

Asp Leu Asp Val Asn Cys Leu Gln Asn Asn Leu Thr
        420                 425
```

<210> SEQ ID NO 13
<211> LENGTH: 2592
<212> TYPE: DNA
<213> ORGANISM: Felis catus
<220> FEATURE:
<221> NAME/KEY: CDS
<222> LOCATION: (1)..(2217)
<223> OTHER INFORMATION:

<400> SEQUENCE: 13

| | | | | | | | | | | | | | | | | |
|---|---|---|---|---|---|---|---|---|---|---|---|---|---|---|---|---|
| atg | ggc | ttt | ggc | tat | gga | cgg | att | agg | tct | gat | ccg | att | aga | gcc | cgg | 48 |
| Met | Gly | Phe | Gly | Tyr | Gly | Arg | Ile | Arg | Ser | Asp | Pro | Ile | Arg | Ala | Arg | |
| 1 | | | | 5 | | | | | 10 | | | | | 15 | | |
| gcc | gtc | ggc | ttc | gcc | ccc | ttg | cct | ggc | gct | gcc | agc | gcc | cgc | ccc | gcc | 96 |
| Ala | Val | Gly | Phe | Ala | Pro | Leu | Pro | Gly | Ala | Ala | Ser | Ala | Arg | Pro | Ala | |
| | | | 20 | | | | | 25 | | | | | 30 | | | |
| ctc | gtg | gac | acc | cgc | aga | cct | ccc | cga | gac | cct | tcc | cct | ccc | cga | aca | 144 |
| Leu | Val | Asp | Thr | Arg | Arg | Pro | Pro | Arg | Asp | Pro | Ser | Pro | Pro | Arg | Thr | |
| | | 35 | | | | | 40 | | | | | 45 | | | | |
| cgg | cat | tgg | cgc | aga | aat | ctg | aga | ggt | ccg | tgc | acc | ccg | ggc | tcg | gct | 192 |
| Arg | His | Trp | Arg | Arg | Asn | Leu | Arg | Gly | Pro | Cys | Thr | Pro | Gly | Ser | Ala | |
| 50 | | | | | 55 | | | | | 60 | | | | | | |
| cat | ttc | cac | agc | tcc | agc | tcg | ggc | ttc | cgc | ccc | ctg | cgg | ccc | ttc | cga | 240 |
| His | Phe | His | Ser | Ser | Ser | Ser | Gly | Phe | Arg | Pro | Leu | Arg | Pro | Phe | Arg | |
| 65 | | | | | 70 | | | | | 75 | | | | | 80 | |
| gcc | ccg | ccc | caa | gct | tgc | ggg | tgt | ctg | ggc | ccc | cgc | ctc | cgt | gct | cgc | 288 |
| Ala | Pro | Pro | Gln | Ala | Cys | Gly | Cys | Leu | Gly | Pro | Arg | Leu | Arg | Ala | Arg | |
| | | | | 85 | | | | | 90 | | | | | 95 | | |
| cgc | gtg | gcg | ggt | ggg | ttc | ctc | gca | ggt | ggg | ggg | ccc | gtg | cca | gct | ctc | 336 |
| Arg | Val | Ala | Gly | Gly | Phe | Leu | Ala | Gly | Gly | Gly | Pro | Val | Pro | Ala | Leu | |
| | | | 100 | | | | | 105 | | | | | 110 | | | |
| cac | ggg | gag | ggc | ggg | ccc | cgc | ccc | aca | ggt | ctc | ccg | ccc | gtg | cac | ctg | 384 |
| His | Gly | Glu | Gly | Gly | Pro | Arg | Pro | Thr | Gly | Leu | Pro | Pro | Val | His | Leu | |
| | | 115 | | | | | 120 | | | | | 125 | | | | |
| tcg | gct | aac | gcc | acg | cac | ggc | gct | gtg | ctc | cgc | acc | cgc | gct | act | cca | 432 |
| Ser | Ala | Asn | Ala | Thr | His | Gly | Ala | Val | Leu | Arg | Thr | Arg | Ala | Thr | Pro | |
| | 130 | | | | | 135 | | | | | 140 | | | | | |
| cgt | ccg | ttt | gtc | tcg | gcg | tcc | cga | gcc | ggg | ggt | acc | gac | tgc | gac | cag | 480 |
| Arg | Pro | Phe | Val | Ser | Ala | Ser | Arg | Ala | Gly | Gly | Thr | Asp | Cys | Asp | Gln | |
| 145 | | | | | 150 | | | | | 155 | | | | | 160 | |
| gac | ccc | cgc | ggc | cct | cgc | gcc | cca | ccc | tgg | gcc | agg | gtc | ccg | ctg | gcc | 528 |
| Asp | Pro | Arg | Gly | Pro | Arg | Ala | Pro | Pro | Trp | Ala | Arg | Val | Pro | Leu | Ala | |
| | | | | 165 | | | | | 170 | | | | | 175 | | |
| tcg | ggt | aca | ggc | gga | gtt | agc | gag | ctg | tgg | caa | ggg | ggc | ggg | gca | gct | 576 |
| Ser | Gly | Thr | Gly | Gly | Val | Ser | Glu | Leu | Trp | Gln | Gly | Gly | Gly | Ala | Ala | |
| | | | 180 | | | | | 185 | | | | | 190 | | | |
| cct | tgc | ccg | cga | ccg | ggg | cgg | ggg | aag | ggg | cgc | gcg | aag | agg | tgg | gat | 624 |
| Pro | Cys | Pro | Arg | Pro | Gly | Arg | Gly | Lys | Gly | Arg | Ala | Lys | Arg | Trp | Asp | |
| | | 195 | | | | | 200 | | | | | 205 | | | | |
| act | tgg | ggg | agg | ccg | agg | ggt | tgg | ggg | cgg | ccc | cgg | ccc | ggg | tgt | ccg | 672 |
| Thr | Trp | Gly | Arg | Pro | Arg | Gly | Trp | Gly | Arg | Pro | Arg | Pro | Gly | Cys | Pro | |
| | 210 | | | | | 215 | | | | | 220 | | | | | |
| gac | aga | gcc | cgt | gag | gct | ggc | agc | gcc | gtc | gag | gcc | cac | gag | cag | gtg | 720 |
| Asp | Arg | Ala | Arg | Glu | Ala | Gly | Ser | Ala | Val | Glu | Ala | His | Glu | Gln | Val | |
| 225 | | | | | 230 | | | | | 235 | | | | | 240 | |
| aag | agc | atc | ctg | gcg | agg | gag | ccg | act | gcc | aac | gaa | acg | agg | gag | aag | 768 |
| Lys | Ser | Ile | Leu | Ala | Arg | Glu | Pro | Thr | Ala | Asn | Glu | Thr | Arg | Glu | Lys | |
| | | | | 245 | | | | | 250 | | | | | 255 | | |
| gcc | ggc | cca | cca | gca | gct | gag | gaa | gac | gag | acc | tcg | tgg | acc | gca | cct | 816 |
| Ala | Gly | Pro | Pro | Ala | Ala | Glu | Glu | Asp | Glu | Thr | Ser | Trp | Thr | Ala | Pro | |
| | | | 260 | | | | | 265 | | | | | 270 | | | |

| | | |
|---|---|---|
| ggc ggt gag cag gcc atg atg ggg cct agt gtc ggg cca gag gag gtg<br>Gly Gly Glu Gln Ala Met Met Gly Pro Ser Val Gly Pro Glu Glu Val<br>              275                    280                    285 | | 864 |
| ctg gag gcg tcg gca gcg gtg acc ggc gca ccc tgg ctg gag gct gac<br>Leu Glu Ala Ser Ala Ala Val Thr Gly Ala Pro Trp Leu Glu Ala Asp<br>              290                    295                    300 | | 912 |
| agc cct ggc ctg ggt gga gtg acc gca gag gcc ggc agc ggc gac acc<br>Ser Pro Gly Leu Gly Gly Val Thr Ala Glu Ala Gly Ser Gly Asp Thr<br>305                    310                    315                    320 | | 960 |
| cag gcc ctt cca gct acg ctc ccg gct ccc aag gag gcc ctg gga cag<br>Gln Ala Leu Pro Ala Thr Leu Pro Ala Pro Lys Glu Ala Leu Gly Gln<br>                    325                    330                    335 | | 1008 |
| tca tcg atg gcc ccc tcc atc ccc aag gct aca gag gcc agc aga cca<br>Ser Ser Met Ala Pro Ser Ile Pro Lys Ala Thr Glu Ala Ser Arg Pro<br>              340                    345                    350 | | 1056 |
| ccc tcc ccc aca cct ggc gac atg ctg agc ccc ggc cca gaa cac ccc<br>Pro Ser Pro Thr Pro Gly Asp Met Leu Ser Pro Gly Pro Glu His Pro<br>                    355                    360                    365 | | 1104 |
| aag gag agt ccc ttg gag gtt tgg ttg aac ctg gga ggc agc aca cat<br>Lys Glu Ser Pro Leu Glu Val Trp Leu Asn Leu Gly Gly Ser Thr His<br>              370                    375                    380 | | 1152 |
| gac cct cat ggg cca gag ccc aca ttc ccc ttt cag ggc aca atg gag<br>Asp Pro His Gly Pro Glu Pro Thr Phe Pro Phe Gln Gly Thr Met Glu<br>385                    390                    395                    400 | | 1200 |
| ccc cag cca gtg tca gat ata att gac atc gac tac ttc gaa gga ttg<br>Pro Gln Pro Val Ser Asp Ile Ile Asp Ile Asp Tyr Phe Glu Gly Leu<br>                          405                    410                    415 | | 1248 |
| gat ggt gag ggc cgt ggt gcc gac ctg gag agc ttc cca ggg tcg cca<br>Asp Gly Glu Gly Arg Gly Ala Asp Leu Glu Ser Phe Pro Gly Ser Pro<br>                    420                    425                    430 | | 1296 |
| gga acc tca gag cac cac cct gat act ggg gga gag acc cct tcc tgg<br>Gly Thr Ser Glu His His Pro Asp Thr Gly Gly Glu Thr Pro Ser Trp<br>              435                    440                    445 | | 1344 |
| agc ctg ctt gac tta tac gat gac ttc acc ccc ttt gat gaa tct gac<br>Ser Leu Leu Asp Leu Tyr Asp Asp Phe Thr Pro Phe Asp Glu Ser Asp<br>              450                    455                    460 | | 1392 |
| ttc tac ccc acc aca tcc ttc tat gat gac ctt gat gaa gag gag gag<br>Phe Tyr Pro Thr Thr Ser Phe Tyr Asp Asp Leu Asp Glu Glu Glu Glu<br>465                    470                    475                    480 | | 1440 |
| gaa gag gat gac aag gat gca gcg gga ggt gaa gac ctg gaa gat gaa<br>Glu Glu Asp Asp Lys Asp Ala Ala Gly Gly Glu Asp Leu Glu Asp Glu<br>                          485                    490                    495 | | 1488 |
| agt gac ctt ctg gtg cct acc gag aag cct ggt ctg ggg ccc ggg act<br>Ser Asp Leu Leu Val Pro Thr Glu Lys Pro Gly Leu Gly Pro Gly Thr<br>                    500                    505                    510 | | 1536 |
| ggc cag cct acc agt cgg tgg cat gct gtg ccc cca cag cat act ctg<br>Gly Gln Pro Thr Ser Arg Trp His Ala Val Pro Pro Gln His Thr Leu<br>              515                    520                    525 | | 1584 |
| ggg atg gtc cct ggc agc agc atc gcc ctc agg ccc cgc cct gga gag<br>Gly Met Val Pro Gly Ser Ser Ile Ala Leu Arg Pro Arg Pro Gly Glu<br>530                    535                    540 | | 1632 |
| cca ggc agg gac ctg acc cca agc gag aat ggc act gag tgc cgc agc<br>Pro Gly Arg Asp Leu Thr Pro Ser Glu Asn Gly Thr Glu Cys Arg Ser<br>545                    550                    555                    560 | | 1680 |
| ggc ttt gtg cga cat aac ggc tcc tgc cgg tca gtg tgc gac ctc ttt<br>Gly Phe Val Arg His Asn Gly Ser Cys Arg Ser Val Cys Asp Leu Phe<br>                    565                    570                    575 | | 1728 |
| cca agt tac tgt cac aat ggc ggc cag tgc tac ctg gtg gag aac ata<br>Pro Ser Tyr Cys His Asn Gly Gly Gln Cys Tyr Leu Val Glu Asn Ile | | 1776 |

```
                580              585              590
ggg gcc ttc tgc agg tgc aac aca cag gac tac atc tgg cac aag ggg      1824
Gly Ala Phe Cys Arg Cys Asn Thr Gln Asp Tyr Ile Trp His Lys Gly
        595                  600                  605 atg cgc tgc gag tcc atc atc acc gac ttc cag gtg atg tgc gtg gcc      1872
Met Arg Cys Glu Ser Ile Ile Thr Asp Phe Gln Val Met Cys Val Ala
610                  615                  620 gtc ggc tcg gct gcc ctt gta ctg ctc ctc ttc atg atg aca gtg          1920
Val Gly Ser Ala Ala Leu Val Leu Leu Leu Phe Met Met Thr Val
625                  630                  635                  640 ttc ttc gcc aag aag cta tat ctg ctc aag aca gag aat acc aag ctg      1968
Phe Phe Ala Lys Lys Leu Tyr Leu Leu Lys Thr Glu Asn Thr Lys Leu
                645                  650                  655 cgt agg acc aac aaa ttc cgg acc ccg tct gaa ctc cac aac gat aac      2016
Arg Arg Thr Asn Lys Phe Arg Thr Pro Ser Glu Leu His Asn Asp Asn
660                  665                  670 ttc tcc ctc tcc acc att gcc gaa ggc tct cac cca aac gat gac cct      2064
Phe Ser Leu Ser Thr Ile Ala Glu Gly Ser His Pro Asn Asp Asp Pro
        675                  680                  685 agt gct ccc cac aaa atc cag gaa gct ctc aag tcc tgc ctg aaa gag      2112
Ser Ala Pro His Lys Ile Gln Glu Ala Leu Lys Ser Cys Leu Lys Glu
690                  695                  700 gag gag tca ttt aac atc cag aac tcc atg tca ccc aaa ctt gag ggt      2160
Glu Glu Ser Phe Asn Ile Gln Asn Ser Met Ser Pro Lys Leu Glu Gly
705                  710                  715                  720 ggc aaa ggt gac cag gct gac ttg gag gtg aac tgt ctt cag aat aac      2208
Gly Lys Gly Asp Gln Ala Asp Leu Glu Val Asn Cys Leu Gln Asn Asn
                725                  730                  735 cta acc taa agcagaacaa gaagagagga aatgggggga gggggggtac              2257
Leu Thr ggggagaaac atgacctcct cttgtacaga gtctatttct tgtaaccatt tgttaaactc    2317 ttttctttt  ctgatctcat ggcatgcttt gatgtatttt gtacaggagg ggaaacacac    2377
acacacacac acacacacac acacacacac acacacacta agcaaagaac ccagacaaaa    2437
ttgcatacgt tgggttgttt tgtctgtgct gtctgtacat tgcttctgct gctgtgattt    2497
ctaaacctac gctgttattc aactactttt tttttgtact ttgacccacc tttttttgaa    2557
ataagagtaa aaacaaagt tcttgaaata aaact                                2592
```

<210> SEQ ID NO 14
<211> LENGTH: 738
<212> TYPE: PRT
<213> ORGANISM: Felis catus

<400> SEQUENCE: 14

Met Gly Phe Gly Tyr Gly Arg Ile Arg Ser Asp Pro Ile Arg Ala Arg
1               5                   10                  15

Ala Val Gly Phe Ala Pro Leu Pro Gly Ala Ala Ser Ala Arg Pro Ala
            20                  25                  30

Leu Val Asp Thr Arg Arg Pro Pro Arg Asp Pro Ser Pro Pro Arg Thr
        35                  40                  45

Arg His Trp Arg Arg Asn Leu Arg Gly Pro Cys Thr Pro Gly Ser Ala
    50                  55                  60

His Phe His Ser Ser Ser Ser Gly Phe Arg Pro Leu Arg Pro Phe Arg
65                  70                  75                  80

Ala Pro Pro Gln Ala Cys Gly Cys Leu Gly Pro Arg Leu Arg Ala Arg
                85                  90                  95

-continued

Arg Val Ala Gly Gly Phe Leu Ala Gly Gly Pro Val Pro Ala Leu
            100                 105                 110
His Gly Glu Gly Gly Pro Arg Pro Thr Gly Leu Pro Pro Val His Leu
            115                 120                 125
Ser Ala Asn Ala Thr His Gly Ala Val Leu Arg Thr Arg Ala Thr Pro
130                 135                 140
Arg Pro Phe Val Ser Ala Ser Arg Ala Gly Gly Thr Asp Cys Asp Gln
145                 150                 155                 160
Asp Pro Arg Gly Pro Arg Ala Pro Pro Trp Ala Arg Val Pro Leu Ala
            165                 170                 175
Ser Gly Thr Gly Gly Val Ser Glu Leu Trp Gln Gly Gly Ala Ala
            180                 185                 190
Pro Cys Pro Arg Pro Gly Arg Gly Lys Gly Arg Ala Lys Arg Trp Asp
            195                 200                 205
Thr Trp Gly Arg Pro Arg Gly Trp Gly Arg Pro Arg Pro Gly Cys Pro
            210                 215                 220
Asp Arg Ala Arg Glu Ala Gly Ser Ala Val Glu Ala His Glu Gln Val
225                 230                 235                 240
Lys Ser Ile Leu Ala Arg Glu Pro Thr Ala Asn Glu Thr Arg Glu Lys
            245                 250                 255
Ala Gly Pro Pro Ala Ala Glu Glu Asp Glu Thr Ser Trp Thr Ala Pro
            260                 265                 270
Gly Gly Glu Gln Ala Met Met Gly Pro Ser Val Gly Pro Glu Glu Val
            275                 280                 285
Leu Glu Ala Ser Ala Ala Val Thr Gly Ala Pro Trp Leu Glu Ala Asp
            290                 295                 300
Ser Pro Gly Leu Gly Gly Val Thr Ala Glu Ala Gly Ser Gly Asp Thr
305                 310                 315                 320
Gln Ala Leu Pro Ala Thr Leu Pro Ala Pro Lys Glu Ala Leu Gly Gln
            325                 330                 335
Ser Ser Met Ala Pro Ser Ile Pro Lys Ala Thr Glu Ala Ser Arg Pro
            340                 345                 350
Pro Ser Pro Thr Pro Gly Asp Met Leu Ser Pro Gly Pro Glu His Pro
            355                 360                 365
Lys Glu Ser Pro Leu Glu Val Trp Leu Asn Leu Gly Gly Ser Thr His
            370                 375                 380
Asp Pro His Gly Pro Glu Pro Thr Phe Pro Phe Gln Gly Thr Met Glu
385                 390                 395                 400
Pro Gln Pro Val Ser Asp Ile Ile Asp Ile Asp Tyr Phe Glu Gly Leu
            405                 410                 415
Asp Gly Glu Gly Arg Gly Ala Asp Leu Glu Ser Phe Pro Gly Ser Pro
            420                 425                 430
Gly Thr Ser Glu His His Pro Asp Thr Gly Glu Thr Pro Ser Trp
            435                 440                 445
Ser Leu Leu Asp Leu Tyr Asp Asp Phe Thr Pro Phe Asp Glu Ser Asp
            450                 455                 460
Phe Tyr Pro Thr Thr Ser Phe Tyr Asp Asp Leu Asp Glu Glu Glu
465                 470                 475                 480
Glu Glu Asp Asp Lys Asp Ala Ala Gly Gly Glu Asp Leu Glu Asp Glu
            485                 490                 495
Ser Asp Leu Leu Val Pro Thr Glu Lys Pro Gly Leu Gly Pro Gly Thr
            500                 505                 510
Gly Gln Pro Thr Ser Arg Trp His Ala Val Pro Pro Gln His Thr Leu

```
                515                 520                 525
Gly Met Val Pro Gly Ser Ser Ile Ala Leu Arg Pro Arg Pro Gly Glu
    530                 535                 540

Pro Gly Arg Asp Leu Thr Pro Ser Glu Asn Gly Thr Glu Cys Arg Ser
545                 550                 555                 560

Gly Phe Val Arg His Asn Gly Ser Cys Arg Ser Val Cys Asp Leu Phe
                565                 570                 575

Pro Ser Tyr Cys His Asn Gly Gly Gln Cys Tyr Leu Val Glu Asn Ile
            580                 585                 590

Gly Ala Phe Cys Arg Cys Asn Thr Gln Asp Tyr Ile Trp His Lys Gly
        595                 600                 605

Met Arg Cys Glu Ser Ile Ile Thr Asp Phe Gln Val Met Cys Val Ala
    610                 615                 620

Val Gly Ser Ala Ala Leu Val Leu Leu Leu Leu Phe Met Met Thr Val
625                 630                 635                 640

Phe Phe Ala Lys Lys Leu Tyr Leu Leu Lys Thr Glu Asn Thr Lys Leu
                645                 650                 655

Arg Arg Thr Asn Lys Phe Arg Thr Pro Ser Glu Leu His Asn Asp Asn
            660                 665                 670

Phe Ser Leu Ser Thr Ile Ala Glu Gly Ser His Pro Asn Asp Asp Pro
        675                 680                 685

Ser Ala Pro His Lys Ile Gln Glu Ala Leu Lys Ser Cys Leu Lys Glu
    690                 695                 700

Glu Glu Ser Phe Asn Ile Gln Asn Ser Met Ser Pro Lys Leu Glu Gly
705                 710                 715                 720

Gly Lys Gly Asp Gln Ala Asp Leu Glu Val Asn Cys Leu Gln Asn Asn
                725                 730                 735

Leu Thr

<210> SEQ ID NO 15
<211> LENGTH: 3881
<212> TYPE: DNA
<213> ORGANISM: Mus musculus
<220> FEATURE:
<221> NAME/KEY: CDS
<222> LOCATION: (1816)..(3516)
<223> OTHER INFORMATION:

<400> SEQUENCE: 15
atttctctgc agggagggga aagatagtt gaggaaggaa atatttcaca ttcgcttgtt      60
tgttctactg atcaaaacag aatttaaaag gatagttacg ggtgggaaat agggtagata     120
gaaggatttg gttggttagt tggttctaga cagggattac agacataagc taccataacc     180
agcaaataca attattttgc agtactagga attgaacctg aagtctcact cattttaggc     240
aagtgctctc cctaactctt aagtgtttta ccataagtag gaaaagactt tattgtgacc     300
atgccctagc atgaaaggac ttacatagga tctcctgtgt ggtaggaact tccaccaaca     360 tccactttg acaactacca cccaggaatt gaagagagaa ataggtatta tatctgggta      420
agcaagcccc ctcttgactg gaactccaaa ctaggacacg tatgtctggt tgccactctc     480
tagatgtcat acagaccta catagccacc tccgagccag gatataagag cctagctgct      540
ggaattttgt cagccttgag gggactctaa gctgcaacca tacttgtgag agaaaaggag     600
tgttgaacca aggcaactca ctagaagaca ggtatgagac agattaaatg atggtcctcc     660
atcttgttca tatttggtca ctgacagaag actatcaaca ccagcatcgc ccttggacta     720
```

```
                                              -continued acccttggac tgagctgaac atgatcattt aggtcgataa taaaacatca atatgtaggc       780
tatttggagg cggggaaagc caggtgacta agctgtagtt ctgcctccct tccaacaggt       840
ctcccagtaa gcagtgaacc tgggttagga acagagacct ctctctccac gttgcatgtg       900
cacctggcag tgatctagac ctcttggttt aaccaggaac ttgggtttgg gtagtactgg       960
tcacctgcgg aaggccgccc tggatttaga aaacgcaagg tggagtccaa atactgggga      1020
ccggataaca cgttgggtgg acctggctgt gcaagattta aactaatggc tttggctgtg      1080
gacagattag gtctgatcca attagagcct aggccgtagt attcgcctcc ttgccaggct      1140
ctgtcgatgt tctccctgct ctccggaaga agacttagag tcggactgga gaaccttctg      1200
gacaccgaat tctggattgg caccggacag tccgtgcccc gggctccgct ctctccacac      1260
tgggggcgcg ggcttccgcc ccctgtggcc cttccgagcc ccgccccgag cctgcgggtg      1320
tcggagcccg cgacgtcccc gcctcccctg cgcgcgcgtg gcgggtgggt tcctcgcagg      1380
tccgcggccc agcgcgctca gcactggaag cgcaagcggg ccccgtgggc tgccgccggt      1440
gcacctgtcg gcttccccca gtggctctgc tgccgcccct gcgcgccgcg cttgcatcgc      1500
tctccacgtc ccgtgccaga ggggtctgac tgtcccctgg cgaggaagac cgagaggggc      1560
cggcgtcaac gcgacgtgct gcggggcggg cggagtgggg gcggcgccga acgcggcagc      1620
ggcaagcggc agcggcggcg cgggaggcgg ggaggcgcgg cgctcggagg acagcggctg      1680
acggcggcat gcggcggctc atgctgccca ccgtgggctg aggcggccgc cacgggcgcg      1740
caggcgcagc ggccgggcaa gccgagggcg cagccaagcc gcgcgcaccg cgcacagcgg      1800 cagggggctcc gcgca atg ggc cga gct gga ggc ggg ggc ccg gac tgg ggg     1851
                  Met Gly Arg Ala Gly Gly Gly Gly Pro Asp Trp Gly
                   1               5                  10 ccg ccg cca gtg ctg ctg ctt ctg ggg gtc acg ctg gtg ctc acc gct       1899
Pro Pro Pro Val Leu Leu Leu Leu Gly Val Thr Leu Val Leu Thr Ala
            15                  20                  25 ggg gcc gta ccg gca cgg gaa aca ggc agt gcg atc gag gct gaa gag       1947
Gly Ala Val Pro Ala Arg Glu Thr Gly Ser Ala Ile Glu Ala Glu Glu
        30                  35                  40 ctg gtg agg agc agc ctg gca tgg gag tcg cgt gcc aat gac acg cgg       1995
Leu Val Arg Ser Ser Leu Ala Trp Glu Ser Arg Ala Asn Asp Thr Arg
45                  50                  55                  60 gag gaa gcc ggc ctg cca gca gct ggg gaa gat gag acc tcg tgg aca       2043
Glu Glu Ala Gly Leu Pro Ala Ala Gly Glu Asp Glu Thr Ser Trp Thr
                65                  70                  75 gag cgg ggc agt gag atg gct gcg gtg ggc cct ggg gtc ggg cca gag       2091
Glu Arg Gly Ser Glu Met Ala Ala Val Gly Pro Gly Val Gly Pro Glu
            80                  85                  90 gag gca cta gag gca tcg gct gca gtg act ggc act gcc tgg cta gag       2139
Glu Ala Leu Glu Ala Ser Ala Ala Val Thr Gly Thr Ala Trp Leu Glu
        95                  100                 105 gca gat ggc cca ggc ctg ggt gga gtg act gca gag gct ggc agt ggc       2187
Ala Asp Gly Pro Gly Leu Gly Gly Val Thr Ala Glu Ala Gly Ser Gly
    110                 115                 120 gac gcc cag acc ctt cca gct acg ctc cag gct cct gat gag gcc ctt       2235
Asp Ala Gln Thr Leu Pro Ala Thr Leu Gln Ala Pro Asp Glu Ala Leu
125                 130                 135                 140 ggg tca tct aca atg ccc cct gcc atc cct gag gct act gaa acc agt       2283
Gly Ser Ser Thr Met Pro Pro Ala Ile Pro Glu Ala Thr Glu Thr Ser
                145                 150                 155 gga cct ccc tcc cct gct gtc cat gat aag cct agt gta ggc cct gaa       2331
Gly Pro Pro Ser Pro Ala Val His Asp Lys Pro Ser Val Gly Pro Glu
            160                 165                 170
```

| | |
|---|---|
| ctc cct aaa gag atc ccc ttg gag gtt cgg ctg aac ctg gga ggc agc<br>Leu Pro Lys Glu Ile Pro Leu Glu Val Arg Leu Asn Leu Gly Gly Ser<br>     175               180              185 | 2379 |
| aca cca gag ccc act ttt ccc ctt cag ggc act ctc gag acc caa cca<br>Thr Pro Glu Pro Thr Phe Pro Leu Gln Gly Thr Leu Glu Thr Gln Pro<br>     190               195              200 | 2427 |
| gcc tca gat ata att gac att gat tac ttt gaa gga ttg gat agt gag<br>Ala Ser Asp Ile Ile Asp Ile Asp Tyr Phe Glu Gly Leu Asp Ser Glu<br>205              210              215              220 | 2475 |
| ggt cgt ggt gca gac atg ggc agc ttc ccg ggg tca cca gga acc tca<br>Gly Arg Gly Ala Asp Met Gly Ser Phe Pro Gly Ser Pro Gly Thr Ser<br>                225              230              235 | 2523 |
| gaa aat cac cct gat acc gaa gga gag acc cct tcc tgg agc ctg ctt<br>Glu Asn His Pro Asp Thr Glu Gly Glu Thr Pro Ser Trp Ser Leu Leu<br>     240               245              250 | 2571 |
| gat ttg tat gat gac ttc acc cct ttt gat gag tct gat ttc tac ccc<br>Asp Leu Tyr Asp Asp Phe Thr Pro Phe Asp Glu Ser Asp Phe Tyr Pro<br>                255              260              265 | 2619 |
| acc aca tcc ttc tat gat gat ttg gaa gag gag gaa gaa gag gag gag<br>Thr Thr Ser Phe Tyr Asp Asp Leu Glu Glu Glu Glu Glu Glu Glu Glu<br>     270               275              280 | 2667 |
| gat aag gat aca gta gga ggt gga gac ctg gaa gat gaa aac gac ctt<br>Asp Lys Asp Thr Val Gly Gly Gly Asp Leu Glu Asp Glu Asn Asp Leu<br>285              290              295              300 | 2715 |
| ctc ctg ccc tct caa aag cct ggt gtg ggg cct ggg aca gga cag ccc<br>Leu Leu Pro Ser Gln Lys Pro Gly Val Gly Pro Gly Thr Gly Gln Pro<br>                305              310              315 | 2763 |
| acc aac cgg tgg cat gct gtt ccc cca cag cat act ctg ggg atg gta<br>Thr Asn Arg Trp His Ala Val Pro Pro Gln His Thr Leu Gly Met Val<br>     320               325              330 | 2811 |
| cct ggc agc agc atc tct ctt agg ccc cgc ccc gga gat cca ggc aag<br>Pro Gly Ser Ser Ile Ser Leu Arg Pro Arg Pro Gly Asp Pro Gly Lys<br>                335              340              345 | 2859 |
| gac ctg gcc tca gga gaa aat ggc aca gag tgc cga gtt ggc ttc gtc<br>Asp Leu Ala Ser Gly Glu Asn Gly Thr Glu Cys Arg Val Gly Phe Val<br>350              355              360 | 2907 |
| agg cac aat ggc tcc tgc cgg tca gtc tgt gac ctc ttt ccg agt tac<br>Arg His Asn Gly Ser Cys Arg Ser Val Cys Asp Leu Phe Pro Ser Tyr<br>365              370              375              380 | 2955 |
| tgt cac aac ggc ggc cag tgc tac ctg gtg gag aac ata ggg gct ttc<br>Cys His Asn Gly Gly Gln Cys Tyr Leu Val Glu Asn Ile Gly Ala Phe<br>                385              390              395 | 3003 |
| tgc agg tgt aac acc cag gac tac atc tgg cac aag ggg atg cgc tgt<br>Cys Arg Cys Asn Thr Gln Asp Tyr Ile Trp His Lys Gly Met Arg Cys<br>     400               405              410 | 3051 |
| gag tcc atc atc acg gac ttc cag gtg atg tgc gtg gcc gtt ggc tcg<br>Glu Ser Ile Ile Thr Asp Phe Gln Val Met Cys Val Ala Val Gly Ser<br>                415              420              425 | 3099 |
| gct gct ctc gtg ctt ctc ctg ttc atg atg act gtg ttc ttt gcc<br>Ala Ala Leu Val Leu Leu Leu Phe Met Met Thr Val Phe Phe Ala<br>     430               435              440 | 3147 |
| aag aag ctc tat ctg ctc aag act gag aat acc aag ctg cgg agg acc<br>Lys Lys Leu Tyr Leu Leu Lys Thr Glu Asn Thr Lys Leu Arg Arg Thr<br>445              450              455              460 | 3195 |
| aat aaa ttc cgg acc cca tct gag ctc cac aac gac aac ttc tcc ctc<br>Asn Lys Phe Arg Thr Pro Ser Glu Leu His Asn Asp Asn Phe Ser Leu<br>                465              470              475 | 3243 |
| tcc acc att gcc gag ggc tct cat cca aat gta agg aaa ttt tgc gac<br>Ser Thr Ile Ala Glu Gly Ser His Pro Asn Val Arg Lys Phe Cys Asp | 3291 |

```
                    480             485             490
act ccc cgt gtc tcc tcc ccc cat gcc cgt gcc ttg gct cac tat gat      3339
Thr Pro Arg Val Ser Ser Pro His Ala Arg Ala Leu Ala His Tyr Asp
        495                 500                 505 aac att gtc tgt cag gac gac ccc agc gct ccc cac aaa atc cag gac      3387
Asn Ile Val Cys Gln Asp Asp Pro Ser Ala Pro His Lys Ile Gln Asp
510                 515                 520 cct ctc aag tcc cgc ctg aag gag gaa gag tcc ttt aac atc cag aac      3435
Pro Leu Lys Ser Arg Leu Lys Glu Glu Glu Ser Phe Asn Ile Gln Asn
525                 530                 535                 540 tcc atg tca ccc aaa ctt gag ggt ggc aaa ggt gac cag gat gac ttg      3483
Ser Met Ser Pro Lys Leu Glu Gly Gly Lys Gly Asp Gln Asp Asp Leu
            545                 550                 555 ggg gtg aac tgt ctg cag aat aac cta acc tga gactgaggaa gaagagagga   3536
Gly Val Asn Cys Leu Gln Asn Asn Leu Thr
                560                 565 aaggggggtg ggggagggaa ggactgttgt ctcctctcgg gcagagtcgg cttcttgtaa    3596
ccatttgtta agcttttctt tttctgatct catggcatgc tctgatgtgt tttgtaggag    3656
gggaaacact taaaataagc aaagaaaccg agcaggattg catatatcgg atggttcttg    3716
tctgtgctct ctgtacgttg cttctgcagc tgtgatttct aaacctctgc tggcactcag    3776 ctgactttt gttttgtact ttgacccgcc tttttttgga ataccaagtt aaaaaaaaaa     3836
agttcttgaa ataaaacttt ttaaaaagct gtccaaaaaa aaaaa                     3881

<210> SEQ ID NO 16
<211> LENGTH: 566
<212> TYPE: PRT
<213> ORGANISM: Mus musculus

<400> SEQUENCE: 16

Met Gly Arg Ala Gly Gly Gly Pro Asp Trp Gly Pro Pro Val
1               5                   10                  15

Leu Leu Leu Leu Gly Val Thr Leu Val Leu Thr Ala Gly Ala Val Pro
                20                  25                  30

Ala Arg Glu Thr Gly Ser Ala Ile Glu Ala Glu Glu Leu Val Arg Ser
            35                  40                  45

Ser Leu Ala Trp Glu Ser Arg Ala Asn Asp Thr Arg Glu Glu Ala Gly
    50                  55                  60

Leu Pro Ala Ala Gly Glu Asp Glu Thr Ser Trp Thr Glu Arg Gly Ser
65                  70                  75                  80

Glu Met Ala Ala Val Gly Pro Gly Val Gly Pro Glu Glu Ala Leu Glu
                85                  90                  95

Ala Ser Ala Ala Val Thr Gly Thr Ala Trp Leu Glu Ala Asp Gly Pro
            100                 105                 110

Gly Leu Gly Gly Val Thr Ala Glu Ala Gly Ser Gly Asp Ala Gln Thr
        115                 120                 125

Leu Pro Ala Thr Leu Gln Ala Pro Asp Glu Ala Leu Gly Ser Ser Thr
    130                 135                 140

Met Pro Pro Ala Ile Pro Glu Ala Thr Glu Thr Ser Gly Pro Pro Ser
145                 150                 155                 160

Pro Ala Val His Asp Lys Pro Ser Val Gly Pro Glu Leu Pro Lys Glu
                165                 170                 175

Ile Pro Leu Glu Val Arg Leu Asn Leu Gly Gly Ser Thr Pro Glu Pro
            180                 185                 190

Thr Phe Pro Leu Gln Gly Thr Leu Glu Thr Gln Pro Ala Ser Asp Ile
```

```
                195                 200                 205
Ile Asp Ile Asp Tyr Phe Glu Gly Leu Asp Ser Glu Gly Arg Gly Ala
210                 215                 220

Asp Met Gly Ser Phe Pro Gly Ser Pro Gly Thr Ser Glu Asn His Pro
225                 230                 235                 240

Asp Thr Glu Gly Glu Thr Pro Ser Trp Ser Leu Leu Asp Leu Tyr Asp
                245                 250                 255

Asp Phe Thr Pro Phe Asp Glu Ser Asp Phe Tyr Pro Thr Thr Ser Phe
            260                 265                 270

Tyr Asp Asp Leu Glu Glu Glu Glu Glu Glu Glu Asp Lys Asp Thr
        275                 280                 285

Val Gly Gly Asp Leu Glu Asp Glu Asn Asp Leu Leu Pro Ser
290                 295                 300

Gln Lys Pro Gly Val Gly Pro Gly Thr Gly Gln Pro Thr Asn Arg Trp
305                 310                 315                 320

His Ala Val Pro Pro Gln His Thr Leu Gly Met Val Pro Gly Ser Ser
                325                 330                 335

Ile Ser Leu Arg Pro Arg Pro Gly Asp Pro Gly Lys Asp Leu Ala Ser
            340                 345                 350

Gly Glu Asn Gly Thr Glu Cys Arg Val Gly Phe Val Arg His Asn Gly
        355                 360                 365

Ser Cys Arg Ser Val Cys Asp Leu Phe Pro Ser Tyr Cys His Asn Gly
370                 375                 380

Gly Gln Cys Tyr Leu Val Glu Asn Ile Gly Ala Phe Cys Arg Cys Asn
385                 390                 395                 400

Thr Gln Asp Tyr Ile Trp His Lys Gly Met Arg Cys Glu Ser Ile Ile
                405                 410                 415

Thr Asp Phe Gln Val Met Cys Val Ala Val Gly Ser Ala Ala Leu Val
            420                 425                 430

Leu Leu Leu Leu Phe Met Met Thr Val Phe Phe Ala Lys Lys Leu Tyr
        435                 440                 445

Leu Leu Lys Thr Glu Asn Thr Lys Leu Arg Arg Thr Asn Lys Phe Arg
450                 455                 460

Thr Pro Ser Glu Leu His Asn Asp Asn Phe Ser Leu Ser Thr Ile Ala
465                 470                 475                 480

Glu Gly Ser His Pro Asn Val Arg Lys Phe Cys Asp Thr Pro Arg Val
                485                 490                 495

Ser Ser Pro His Ala Arg Ala Leu Ala His Tyr Asp Asn Ile Val Cys
            500                 505                 510

Gln Asp Asp Pro Ser Ala Pro His Lys Ile Gln Asp Pro Leu Lys Ser
        515                 520                 525

Arg Leu Lys Glu Glu Glu Ser Phe Asn Ile Gln Asn Ser Met Ser Pro
530                 535                 540

Lys Leu Glu Gly Gly Lys Gly Asp Gln Asp Asp Leu Gly Val Asn Cys
545                 550                 555                 560

Leu Gln Asn Asn Leu Thr
                565

<210> SEQ ID NO 17
<211> LENGTH: 20
<212> TYPE: DNA
<213> ORGANISM: Artificial
<220> FEATURE:
<223> OTHER INFORMATION: T3 primer
```

```
<400> SEQUENCE: 17
aattaaccct cactaaaggg                                                  20

<210> SEQ ID NO 18
<211> LENGTH: 19
<212> TYPE: DNA
<213> ORGANISM: Artificial
<220> FEATURE:
<223> OTHER INFORMATION: T7 primer

<400> SEQUENCE: 18
taatacgact cactatagg                                                   19

<210> SEQ ID NO 19
<211> LENGTH: 20
<212> TYPE: DNA
<213> ORGANISM: Artificial
<220> FEATURE:
<223> OTHER INFORMATION: canis RT primer sense

<400> SEQUENCE: 19
aagttactgt cacaacggcg                                                  20

<210> SEQ ID NO 20
<211> LENGTH: 20
<212> TYPE: DNA
<213> ORGANISM: Artificial
<220> FEATURE:
<223> OTHER INFORMATION: canis RT primer antisense

<400> SEQUENCE: 20
tcatcatgaa gagcaggagc                                                  20

<210> SEQ ID NO 21
<211> LENGTH: 21
<212> TYPE: DNA
<213> ORGANISM: Artificial
<220> FEATURE:
<223> OTHER INFORMATION: human RT primer sense

<400> SEQUENCE: 21
aagttactgt cacaatggcg g                                                21

<210> SEQ ID NO 22
<211> LENGTH: 20
<212> TYPE: DNA
<213> ORGANISM: Artificial
<220> FEATURE:
<223> OTHER INFORMATION: human RT primer antisense

<400> SEQUENCE: 22
tcatcatgaa gagcaggagc                                                  20

<210> SEQ ID NO 23
<211> LENGTH: 20
<212> TYPE: DNA
<213> ORGANISM: Artificial
<220> FEATURE:
<223> OTHER INFORMATION: mouse RT primer sense

<400> SEQUENCE: 23
gagttactgt cacaacggcg                                                  20

<210> SEQ ID NO 24
<211> LENGTH: 20
```

<212> TYPE: DNA
<213> ORGANISM: Artificial
<220> FEATURE:
<223> OTHER INFORMATION: mouse RT primer antisense

<400> SEQUENCE: 24
tcatcatgaa caggaggaga                                           20

<210> SEQ ID NO 25
<211> LENGTH: 18
<212> TYPE: DNA
<213> ORGANISM: Artificial
<220> FEATURE:
<223> OTHER INFORMATION: GAPDH primer

<400> SEQUENCE: 25
gggctgcttt taactctg                                             18

<210> SEQ ID NO 26
<211> LENGTH: 18
<212> TYPE: DNA
<213> ORGANISM: Artificial
<220> FEATURE:
<223> OTHER INFORMATION: GAPDH primer

<400> SEQUENCE: 26
ccaggaaatg agcttgac                                             18

<210> SEQ ID NO 27
<211> LENGTH: 20
<212> TYPE: DNA
<213> ORGANISM: Artificial
<220> FEATURE:
<223> OTHER INFORMATION: GAPDH primer

<400> SEQUENCE: 27
cttcaccacc atggagaagg                                           20

<210> SEQ ID NO 28
<211> LENGTH: 20
<212> TYPE: DNA
<213> ORGANISM: Artificial
<220> FEATURE:
<223> OTHER INFORMATION: GAPDH primer

<400> SEQUENCE: 28
tgaagtcgca ggagacaacc                                           20

<210> SEQ ID NO 29
<211> LENGTH: 30
<212> TYPE: DNA
<213> ORGANISM: Artificial
<220> FEATURE:
<223> OTHER INFORMATION: mus-fullCSPG5 primer sense

<400> SEQUENCE: 29

```
atgggccgag ctggaggcgg gggcccggac                              30

<210> SEQ ID NO 30
<211> LENGTH: 30
<212> TYPE: DNA
<213> ORGANISM: Artificial
<220> FEATURE:
<223> OTHER INFORMATION: mus-fullCSPG5 primer antisense

<400> SEQUENCE: 30
tcaggttagg ttattctgca gacagttcac                              30
```